United States Patent [19]

Katsuda et al.

[11] 4,431,668

[45] Feb. 14, 1984

[54] CYCLOPROPANE CARBOXYLIC ACID ESTER DERIVATIVES

[75] Inventors: Yoshio Katsuda, Nishinomiya; Yoshihiro Minamite, Osaka, both of Japan

[73] Assignee: Dainippon Jochugiku Kabushiki Kaisha, Osaka, Japan

[21] Appl. No.: 960,638

[22] Filed: Nov. 14, 1978

[30] Foreign Application Priority Data

| | | |
|---|---|---|
| Dec. 1, 1977 [JP] | Japan | 52-144712 |
| Jan. 21, 1978 [JP] | Japan | 53-5717 |
| Mar. 1, 1978 [JP] | Japan | 53-23913 |
| Mar. 7, 1978 [JP] | Japan | 53-25834 |
| Mar. 8, 1978 [JP] | Japan | 53-26767 |
| Apr. 1, 1978 [JP] | Japan | 53-38581 |
| Apr. 1, 1978 [JP] | Japan | 53-38583 |
| Oct. 12, 1978 [JP] | Japan | 53-125984 |
| Oct. 24, 1978 [JP] | Japan | 53-130745 |

[51] Int. Cl.³ .................. A01N 37/34; A01N 53/00; C07C 69/757; C07C 121/75
[52] U.S. Cl. .................. 424/304; 260/465 D; 424/274; 424/285; 424/305; 424/308; 548/513; 549/462; 549/467; 549/479; 549/491; 549/501; 560/65; 560/73; 560/118; 560/124
[58] Field of Search ............ 260/465 D, 326 A, 347.4, 260/346.22; 560/121, 123, 124, 61; 424/304, 305

[56] References Cited

U.S. PATENT DOCUMENTS 3,847,944 11/1974 Ohno et al. .................. 560/124 X

OTHER PUBLICATIONS

Wenbert et al., Chemical Abstracts, vol. 74, 42507d, (1971).
Smejkal et al., Chemical Abstract, vol. 54, 24436–24437, (1960).
Julia et al., Chemical Abstracts, vol. 50, 5228–5229, (1956).
Julia et al., Bull. Soc. Chim., France, pp. 734–742, (1966).

Primary Examiner—Dolph H. Torrence
Attorney, Agent, or Firm—Quaintance & Murphy

[57] ABSTRACT

Cyclopropane carboxylic acid ester derivatives and optical and geometrical isomers thereof expressed by the general formula:

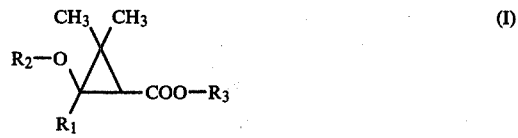

wherein $R_1$ represents hydrogen atom or methyl group, $R_2$ represents alkyl group, alkenyl group, haloalkyl group, haloalkenyl group having 1-6 carbon atoms and a group selected from the groups of the general formulae (II), (III) and (IV):

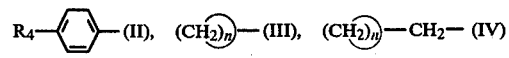

in which n is an integer of 2–5, $R_4$ represents methyl group, chlorine atom or methoxy group, and $R_3$ represents a group selected from the groups of the general formulae (V), (VI), (VII), (VIII), (IX) and (X):

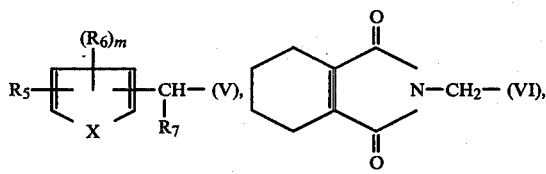

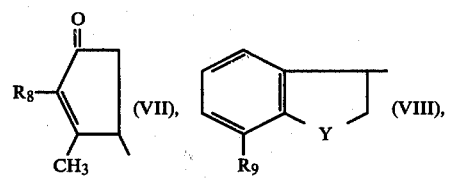

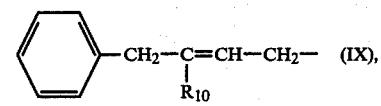

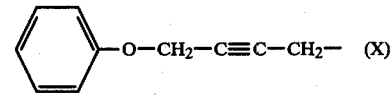

in which X represents oxygen atom or vinylene group, $R_5$ represents allyl group, propargyl group, benzyl group, phenoxy group or 2,2-dichlorovinyloxy group, $R_6$ represents hydrogen atom, methyl group or halogen atom, $R_7$ represents hydrogen atom, cyano group, ethynyl group or trifluoromethyl group and m is an integer of 1–2, $R_8$ represents allyl group or alkadienyl group, Y represents oxygen atom or methylene group, $R_9$ represents hydrogen atom, methyl group, allyl group or halogen atom and $R_{10}$ represents methyl group or halogen atom.

19 Claims, No Drawings

CYCLOPROPANE CARBOXYLIC ACID ESTER DERIVATIVES

DETAILED DESCRIPTION OF THE INVENTION

The present invention relates to novel cyclopropane carboxylic acid ester derivatives and the optical and geometrical isomers thereof expressed by the general formula:

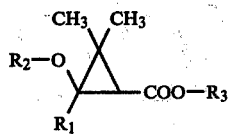

wherein $R_1$ represents hydrogen atom or methyl group, $R_2$ represents alkyl group, alkenyl group, haloalkyl group, haloalkenyl group having 1-6 carbon atoms and a group selected from the groups of the general formulae (II), (III) and (IV):

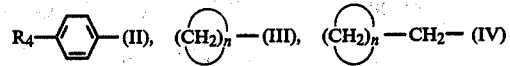

in which n is an integer of 2-5, $R_4$ represents methyl group, chlorine atom or methoxy group, and $R_3$ represents a group selected from the groups of the general formulae (V), (VI), (VII), (VIII), (IX) and (X)

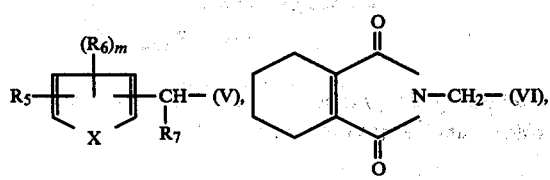

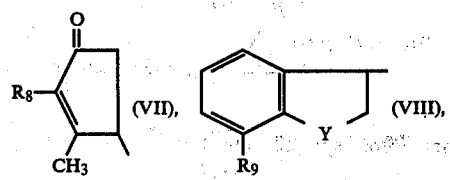

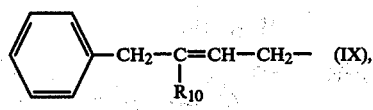

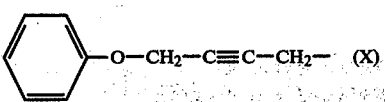

in which X represents oxygen atom or vinylene group, $R_5$ represents allyl group, propargyl group, benzyl group, phenoxy group or 2,2-dichlorovinyloxy group, $R_6$ represents hydrogen atom, methyl group or halogen atom, $R_7$ represents hydrogen atom, cyano group, ethynyl group or trifluoromethyl group and m is an integer of 1-2, $R_8$ represents allyl group or alkadienyl group, Y represents oxygen atom or methylene group, $R_9$ represents hydrogen atom, methyl group, allyl group or halogen atom and $R_{10}$ represents methyl group or halogen atom.

Further, the invention relates to the process for producing said cyclopropane carboxylic acid ester derivatives or steric isomer thereof and to insecticides containing it as active ingredient.

Various alcohol components in chrysanthemumic acid esters have been studied and put into practical use. Such chrysanthemumic acid esters are liable to be decomposed by oxidation with light and therefore the use thereof in the open air has been limited. Recently, studies on acid components in chrysanthemumic acid esters have been extensively made and then compounds produced by substituting the methyl group by halogen atom were found to be stable against light when compared to the conventionally used pyrethroid. However, taking the environmental pollution and chronic toxicity into account, insecticides having the structures similar to those of natural organic compounds consisting of carbon, hydrogen, oxygen and nitrogen will be advantageously used in the future. The present inventors have intensively investigated on the insecticides and found out that the compounds expressed by the abovementioned formula (I) show remarkably strong insecticidal effect against various sanitary and agricultural pests, and that they are far more stable against light than the conventional pyrethroids and show extremely low toxicity to warm blooded animals.

Thus, the compounds expressed by the formula (I) obviate the defect of pyrethroids which are unstable to light, and are excellent insecticide having wide insecticidal spectrum and low toxicity. Furthermore, the cyclopropane carboxylic acids constituting the compounds of formula (I) are easily produced at a low price.

The present invention has been accomplished based on the knowledge mentioned above. The compounds of the formula (I) used as active ingredient in the present invention can be produced according to the ordinary processes for producing esters by reacting a carboxylic acid or a reactive derivative thereof having the general formula (XIII)

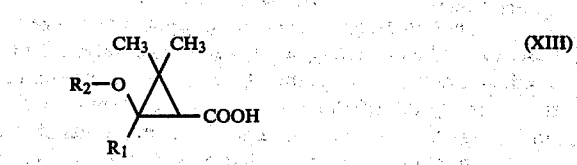

wherein $R_1$ represents hydrogen atom or methyl group, $R_2$ represents alkyl group, alkenyl group, haloalkyl group, haloalkenyl group having 1-6 carbon atoms and a group selected from the groups of the general formulae (II), (III) and (IV):

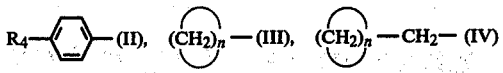

in which n is an integer of 2-5, $R_4$ represents methyl group, chlorine atom or methoxy group, with an alcohol or a reactive derivative thereof expressed by the formula (XIV):

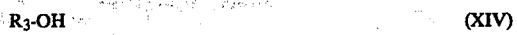

wherein $R_3$ represents a group selected from the groups of the general formulae (V), (VI), (VII), (VIII), (IX) and (X)

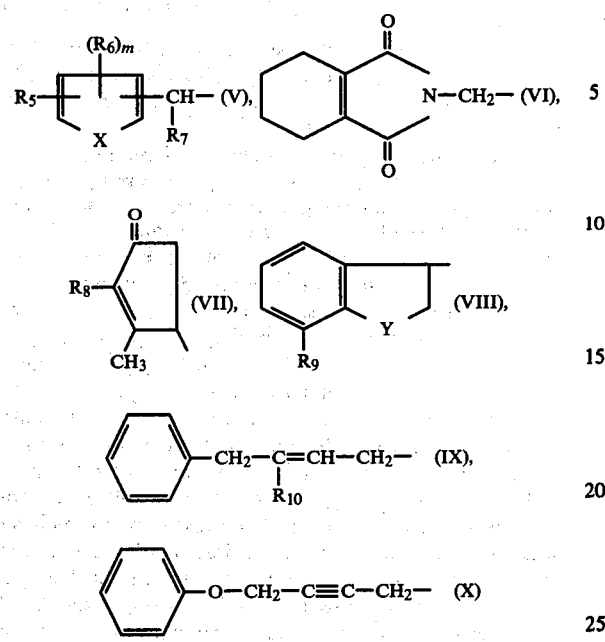

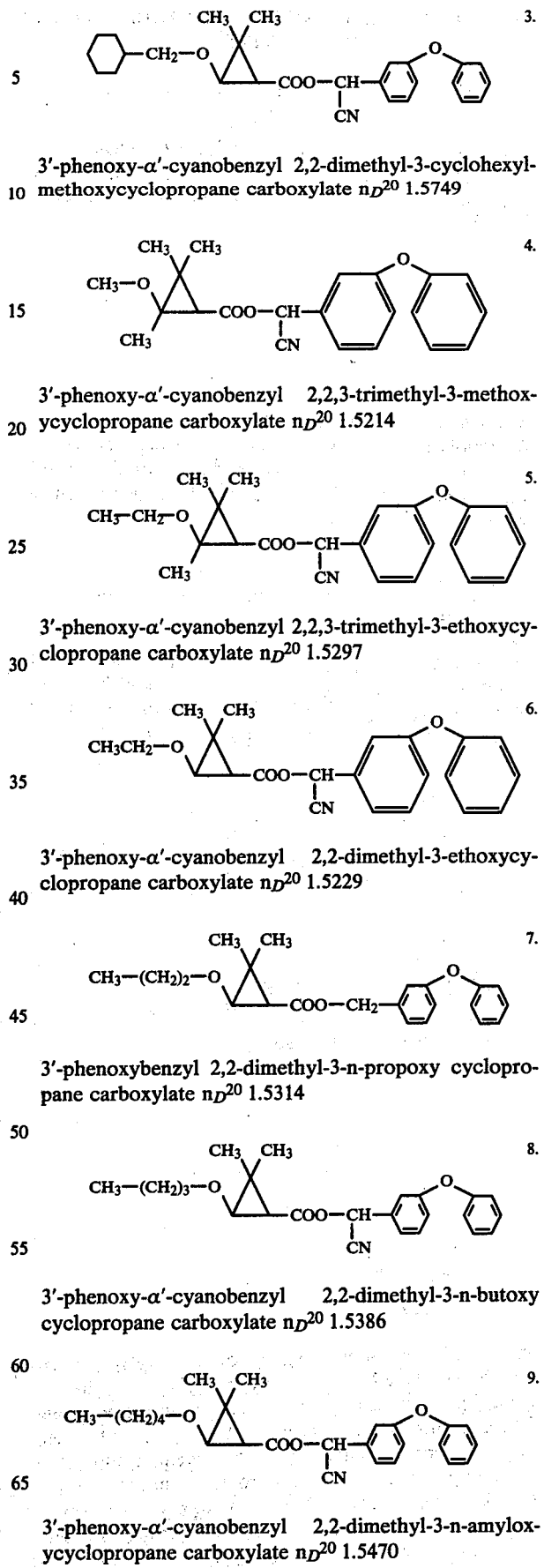

in which X represents oxygen atom or vinylene group, R₅ represents allyl group, propargyl group, benzyl group, phenoxy group or 2,2-dichlorovinyloxy group, R₆ represents hydrogen atom, methyl group or halogen atom, R₇ represents hydrogen atom, cyano group, ethynyl group or trifluoromethyl group and m is an integer of 1–2, R₈ represents allyl group or alkadienyl group, Y represents oxygen atom or methylene group, R₉ represents hydrogen atom, methyl group, allyl group or halogen atom and R₁₀ represents methyl group or halogen atom.

Reactive derivatives of carboxylic acid are, for example, acid halides, acid anhydrides, lower alkyl esters and alkali metal salts. Reactive derivative of alcohol is, for example, chloride. The reaction is carried out in a suitable solvent in the presence of organic or inorganic base, or acid as deacidificating agent or catalyst, if desired, and at elevated temperature at need. Representative compounds of the formula (I) are shown in the following. As a matter of course, the compounds of the present invention are not limited only to the following ones.

1.

3′-phenoxy-α′-cyanobenzyl 2,2-dimethyl-3-isopropoxycyclopropane carboxylate $n_D^{20}$ 1.5204

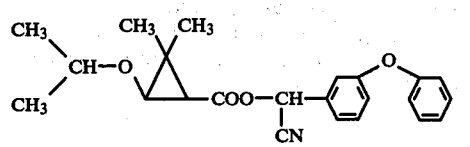

2.

3′-phenoxy-α′-cyanobenzyl 2,2-dimethyl-3-isobutoxycyclopropane carboxylate $n_D^{20}$ 1.5381

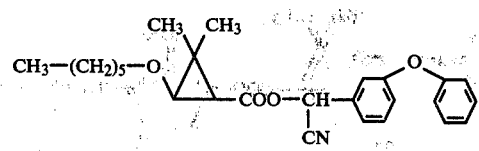

10.

3'-phenoxy-α'-cyanobenzyl 2,2-dimethyl-3-n-hexyloxycyclopropane carboxylate $n_D^{20}$ 1.5594

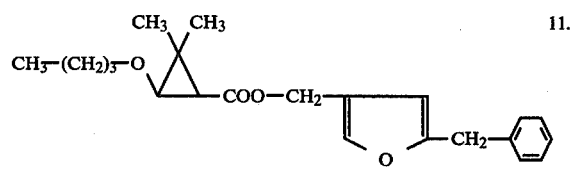

11.

5'-benzyl-3'-furylmethyl 2,2-dimethyl-3-n-butoxycyclopropane carboxylate $n_D^{20}$ 1.5561

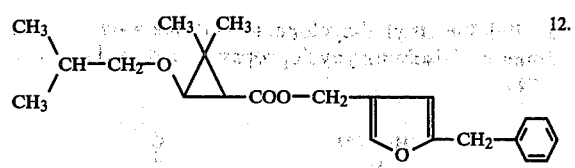

12.

5'-benzyl-3'-furylmethyl 2,2-dimethyl-3-isobutoxycyclopropane carboxylate $n_D^{20}$ 1.5548

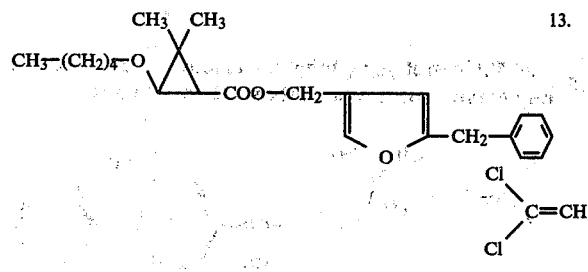

13.

5'-benzyl-3'-furylmethyl 2,2-dimethyl-3-n-amyloxycyclopropane carboxylate $n_D^{20}$ 1.5603

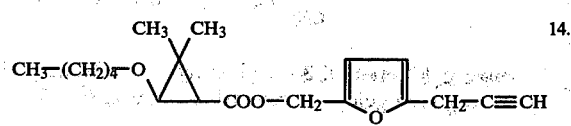

14.

5'-propargyl-2'-furylmethyl 2,2-dimethyl-3-n-amyloxycyclopropane carboxylate $n_D^{20}$ 1.5584

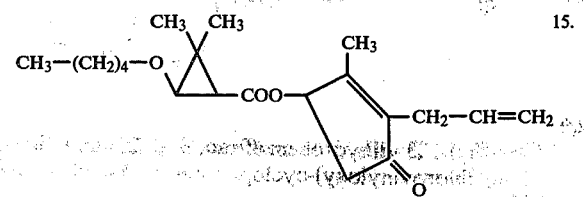

15.

2'-allyl-3'-methyl-2'-cyclopentene-1'-one-4'-yl 2,2-dimethyl-3-n-amyloxycyclopropane carboxylate $n_D^{20}$ 1.5570

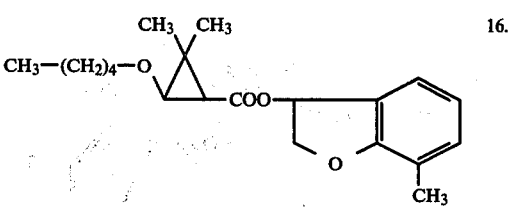

16.

7'-methyl-2',3'-dihydrobenzofuran-3'-yl 2,2-dimethyl-3-n-amyloxycyclopropane carboxylate $n_D^{20}$ 1.5568

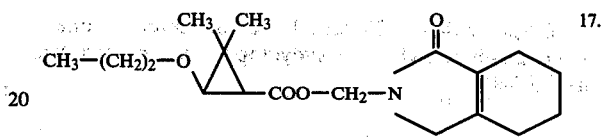

17.

3',4',5',6'-tetrahydrophthalimidemethyl 2,2-dimethyl-3-n-propoxycyclopropane carboxylate $n_D^{20}$ 1.5451

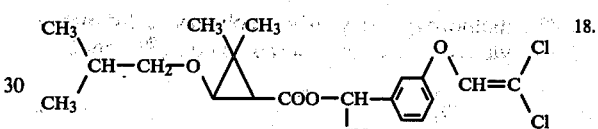

18.

3'-(2,2-dichlorovinyloxy)-α'-cyanobenzyl 2,2-dimethyl-3-isobutoxycyclopane carboxylate $n_D^{20}$ 1.5587

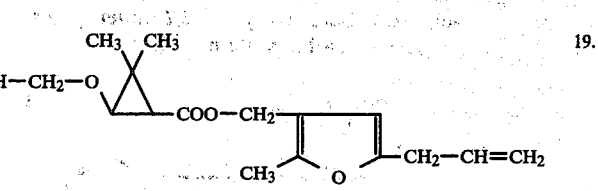

19.

5'-allyl-2'-methyl-3'-furylmethyl 2,2-dimethyl-3-(3,3-dichloroallyloxy)-cyclopropane carboxylate $n_D^{20}$ 1.5622

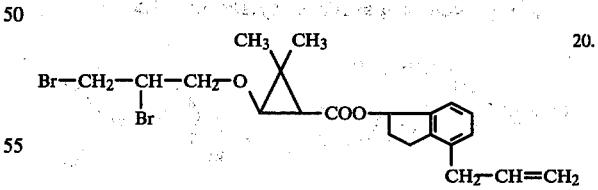

20.

7'-allyl-indane-3'-yl 2,2-dimethyl-3-(2,3-dibromo-n-propoxy)-cyclopropane carboxylate $n_D^{20}$ 1.5704

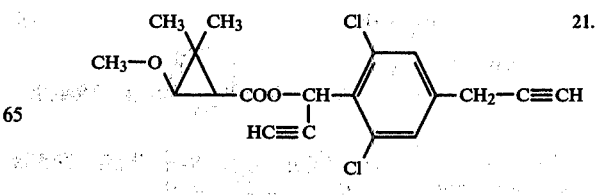

21.

2',6'-dichloro-4'-propargyl-α'-ethynylbenzyl 2,2-dimethyl-3-methoxycyclopropane carboxylate $n_D^{20}$ 1.5488

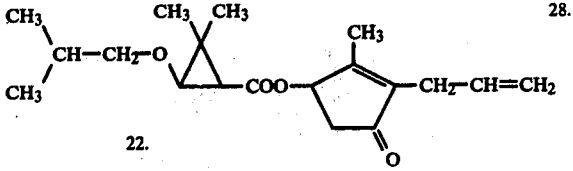

22.

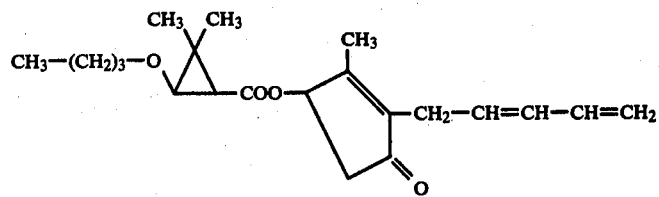

2'-(2,4-pentadienyl)-3'-methyl-2'-cyclopentene-1'-one-4'-yl 2,2-dimethyl-3-butoxycyclopropane carboxylate $n_D^{20}$ 1.5603

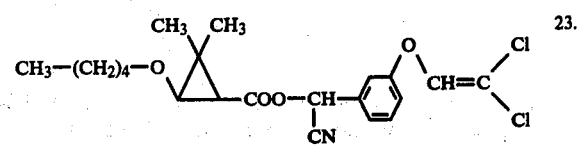

23.

2'-allyl-3'-methyl-2'-cyclopentene-1'-one-4'-yl 2,2-dimethyl-3-isobutoxycyclopropane carboxylate $n_D^{20}$ 1.5496

3'-(2,2-dichlorovinyloxy)-α'-cyanobenzyl 2,2-dimethyl-3-n-amyloxycyclopropane carboxylate $n_D^{20}$ 1.5662

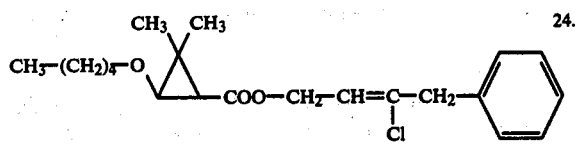

24.

3',4',5',6'-tetrahydrophthalimidemethyl 2,2-dimethyl-3-n-butoxycyclopropane carboxylate $n_D^{20}$ 1.5546

4'-phenyl-3'-chloro-2'-butene-1'-yl 2,2-dimethyl-3-n-amyloxycyclopropane carboxylate $n_D^{20}$ 1.5578

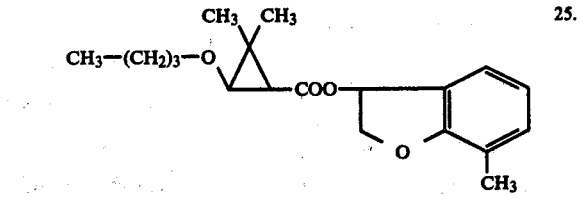

25.

30.

3'-benzyl-α'-cyanobenzyl 2,2-dimethyl-3-(2,2-dichloroethoxy)-cyclopropane carboxylate $n_D^{20}$ 1.5826

7'-methyl-2',3'-dihydrobenzofuran-3'-yl 2,2-dimethyl-3-n-butoxy cyclopropanecarboxylate $n_D^{20}$ 1.5527

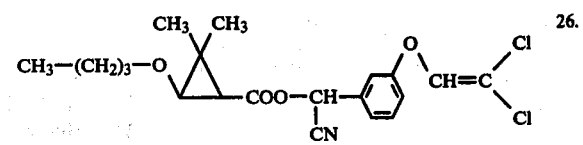

26.

31.

5'-propargyl-2'-methyl-3'-furylmethyl 2,2-dimethyl-3-cyclopropoxy cyclopropane carboxylate $n_D^{20}$ 1.5504

3'-(2,2-dichlorovinyloxy)-α'-cyanobenzyl 2,2-dimethyl-3-n-butoxycyclopropane carboxylate $n_D^{20}$ 1.5600

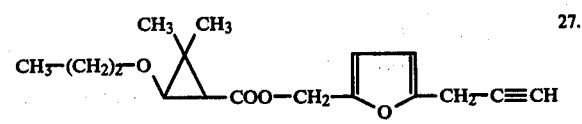

27.

32.

5'-propargyl-2'-furylmethyl 2,2-dimethyl-3-n-propoxycyclopropane carboxylate $n_D^{20}$ 1.5474

7'-methyl-2',3'-dihydrobenzofuran-3'-yl 2,2-dimethyl-3-(2,2-dichlorovinyloxy)-cyclopropane carboxylate $n_D^{20}$ 1.5615

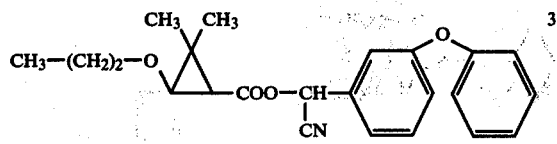

33.

3'-phenoxy-α'-cyanobenzyl 2,2-dimethyl-3-n-propoxycyclopropane carboxylate $n_D^{20}$ 1.5326

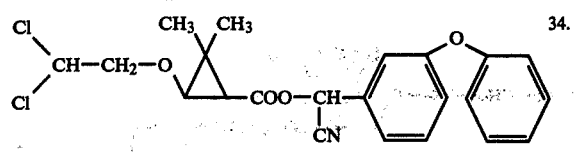

34.

3'-phenoxy-α'-cyanobenzyl 2,2-dimethyl-3-(2,2-dichloroethoxy)-cyclopropane carboxylate $n_D^{20}$ 1.5473

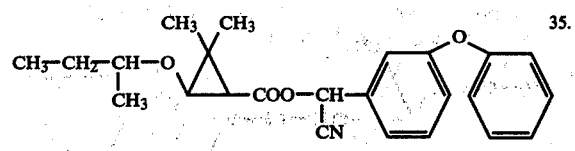

35.

3'-phenoxy-α'-cyanobenzyl 2,2-dimethyl-3-(1-methyl-n-propoxy)-cyclopropane carboxylate $n_D^{20}$ 1.5423

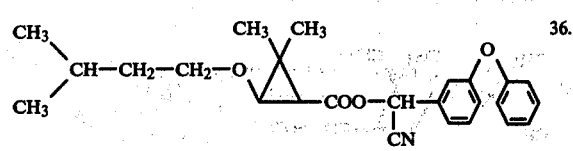

36.

3'-phenoxy-α'-cyanobenzyl 2,2-dimethyl-3-isoamyloxycyclopropane carboxylate $n_D^{20}$ 1.5469

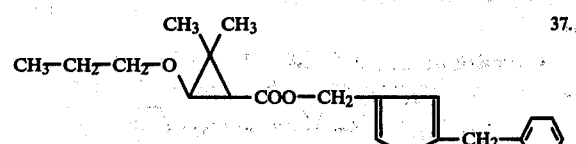

37.

5'-benzyl-3'-furylmethyl 2,2-dimethyl-3-n-propoxycyclopropane carboxylate $n_D^{20}$ 1.5502

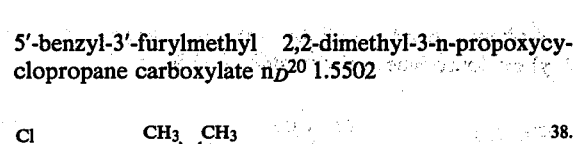

38.

5'-benzyl-3'-furylmethyl 2,2-dimethyl-3-(2,2-dichloroethoxy)-cyclopropane carboxylate $n_D^{20}$ 1.5671

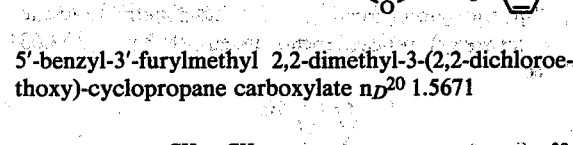

39.

3'-phenoxybenzyl 2,2-dimethyl-3-isobutoxycyclopropane carboxylate $n_D^2$ 1.5327

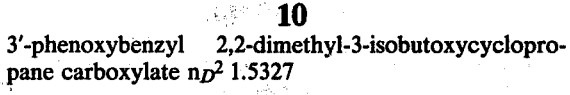

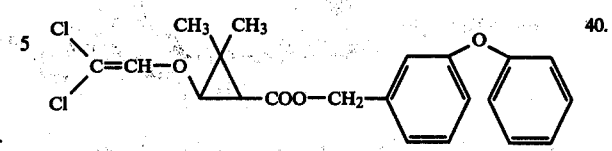

40.

3'-phenoxybenzyl 2,2-dimethyl-3-(2,2-dichlorovinyloxy)-cyclopropane carboxylate $n_D^{20}$ 1.5435

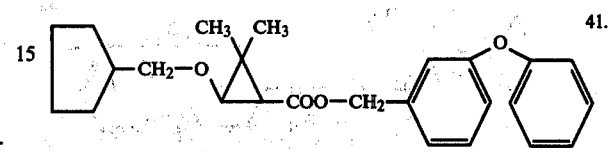

41.

3'-phenoxybenzyl 2,2-dimethyl-3-cyclopentylmethoxycyclopropane carboxylate $n_D^{20}$ 1.5471

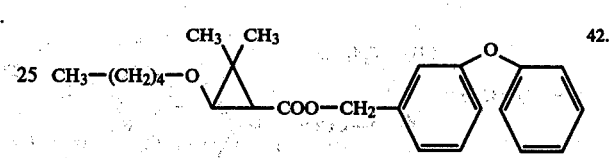

42.

3'-phenoxybenzyl 2,2-dimethyl-3-n-amyloxycyclopropane carboxylate $n_D^{20}$ 1.5439

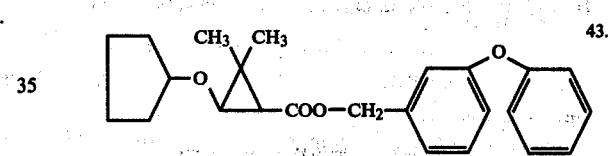

43.

3'-phenoxybenzyl 2,2-dimethyl-3-cyclopentyloxycyclopropane carboxylate $n_D^{20}$ 1.5434

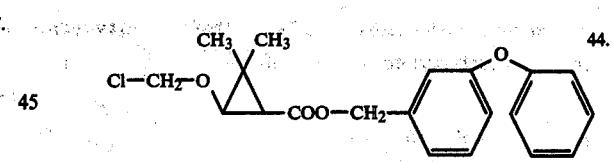

44.

3'-phenoxybenzyl 2,2-dimethyl-3-chloromethoxycyclopropane carboxylate $n_D^{20}$ 1.5294

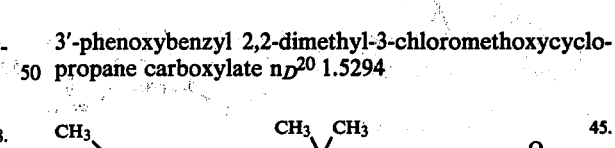

45.

3'-phenoxybenzyl 2,2-dimethyl-3-isoamyloxycyclopropane carboxylate $n_D^{20}$ 1.5401

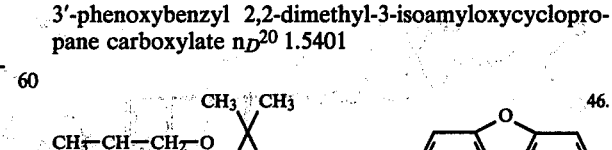

46.

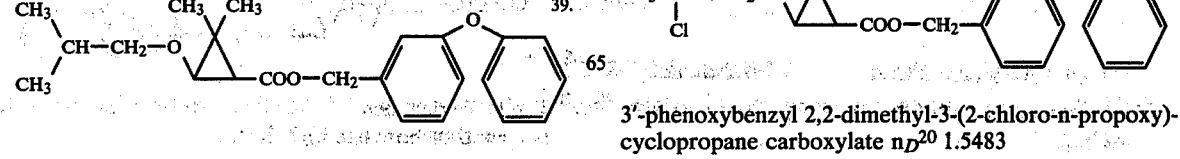

3'-phenoxybenzyl 2,2-dimethyl-3-(2-chloro-n-propoxy)-cyclopropane carboxylate $n_D^{20}$ 1.5483

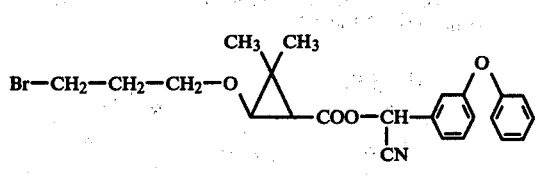

3'-phenoxy-α'-cyanobenzyl 2,2-dimethyl-3-(3-bromo-n-propoxy)-cyclopropane carboxylate $n_D^{20}$ 1.5606

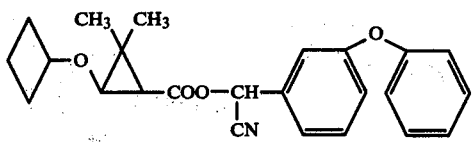

3'-phenoxy-α'-cyanobenzyl 2,2-dimethyl-3-cyclobutoxycyclopropane carboxylate $n_D^{20}$ 1.5427

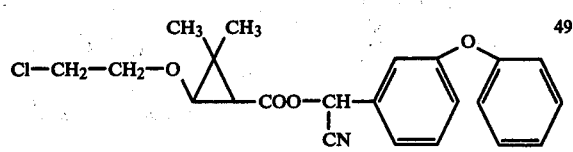

3'-phenoxy-α'-cyanobenzyl 2,2-dimethyl-3-(2-chloroethoxy)-cyclopropane carboxylate $n_D^{20}$ 1.5451

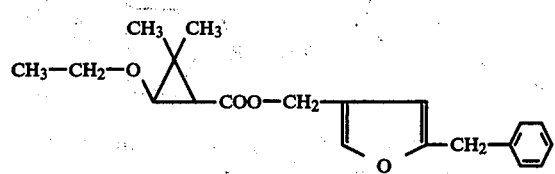

5'-benzyl-3'-furylmethyl 2,2-dimethyl-3-ethoxycyclopropane carboxylate $n_D^{20}$ 1.5450

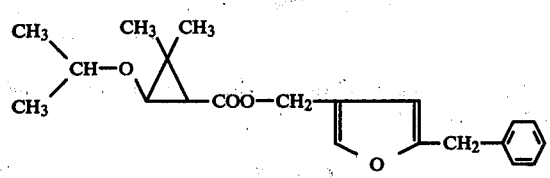

5'-benzyl-3'-furylmethyl 2,2-dimethyl-3-isopropoxycyclopropane carboxylate $n_D^{20}$ 1.5497

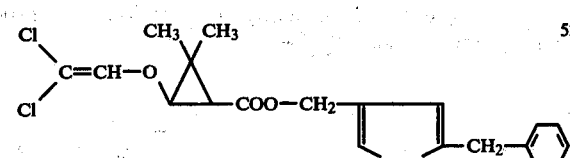

5'-benzyl-3'-furylmethyl 2,2-dimethyl-3-(2,2-dichlorovinyloxy)-cyclopropane carboxylate $n_D^{20}$ 1.5623

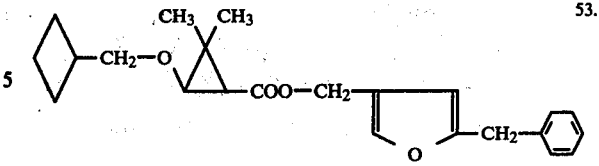

5'-benzyl-3'-furylmethyl 2,2-dimethyl-3-cyclobutylmethoxycyclopropane carboxylate $n_D^{20}$ 1.5612

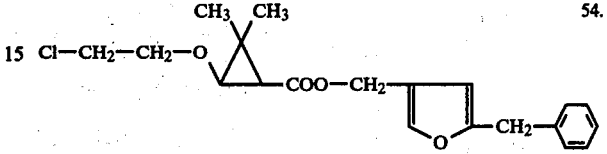

5'-benzyl-3'-furylmethyl 2,2-dimethyl-3-(2-chloroethoxy)-cyclopropane carboxylate $n_D^{20}$ 1.5586

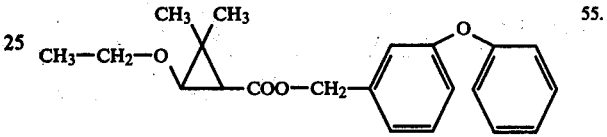

3'-phenoxybenzyl 2,2-dimethyl-3-ethoxycyclopropane carboxylate $n_D^{20}$ 1.5238

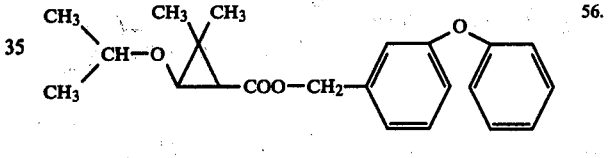

3'-phenoxybenzyl 2,2-dimethyl-3-isopropoxycyclopropane carboxylate $n_D^{20}$ 1.5288

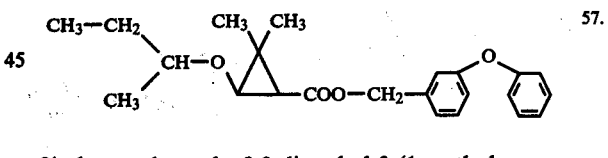

3'-phenoxybenzyl 2,2-dimethyl-3-(1-methyl-n-propoxy)-cyclopropane carboxylate $n_D^{20}$ 1.5346

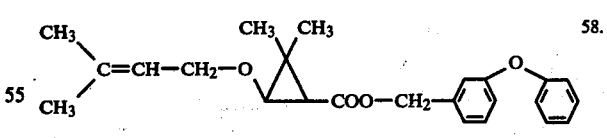

3'-phenoxybenzyl 2,2-dimethyl-3-(3-methyl-2-butenyloxy)-cyclopropane carboxylate $n_D^{20}$ 1.5345

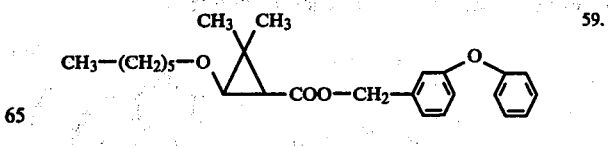

3'-phenoxybenzyl 2,2-dimethyl-3-n-hexyloxycyclopropane carboxylate $n_D^{20}$ 1.5493

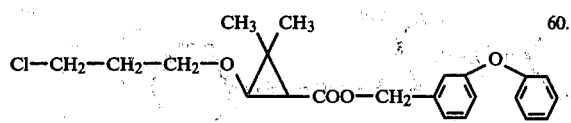

3'-phenoxybenzyl 2,2-dimethyl-3-(3-chloro-n-propoxy)-cyclopropane carboxylate $n_D^{20}$ 1.5406

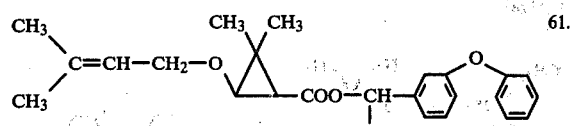

3'-phenoxy-α'-cyanobenzyl 2,2-dimethyl-3-(3-methyl-2-butenyloxy)-cyclopropane carboxylate $n_D^{20}$ 1.5540

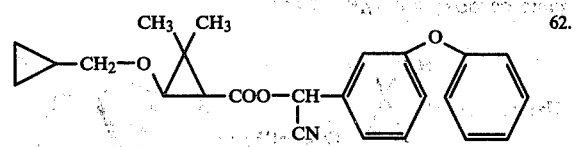

3'-phenoxy-α'-cyanobenzyl 2,2-dimethyl-3-cyclopropylmethoxycyclopropane carboxylate $n_D^{20}$ 1.5409

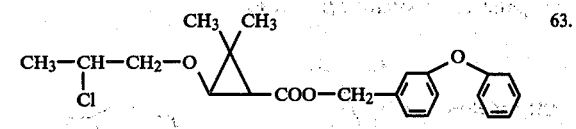

3'-phenoxy-α'-cyanobenzyl 2,2-dimethyl-3-(2-chloro-n-propoxy)-cyclopropane carboxylate $n_D^{20}$ 1.5536

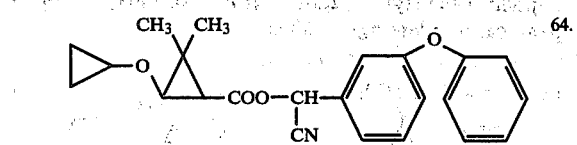

3'-phenoxy-α'-cyanobenzyl 2,2-dimethyl-3-cyclopropoxycyclopropane carboxylate $n_D^{20}$ 1.5419.

3'-phenoxybenzyl 2,2-dimethyl-3-n-butoxycyclopropane carboxylate $n_D^{20}$ 1.5339

3'-phenoxybenzyl 2,2-dimethyl-3-allyloxycyclopropane carboxylate $n_D^{20}$ 1.5275

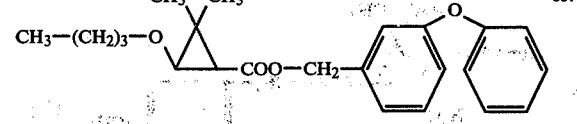

3'-phenoxybenzyl 2,2-dimethyl-3-(2,2-dichloroethoxy)-cyclopropane carboxylate $n_D^{20}$ 1.5420

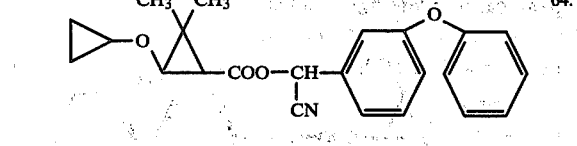

3'-phenoxy-α'-cyanobenzyl 2,2-dimethyl-3-(2,2-dichlorovinyloxy)-cyclopropane carboxylate $n_D^{20}$ 1.5481

3'-phenoxy-α'-cyanobenzyl 2,2-dimethyl-3-allyloxycyclopropane carboxylate $n_D^{20}$ 1.5364

3'-phenoxybenzyl 2,2-dimethyl-3-(2-chloroethoxy)-cyclopropane carboxylate $n_D^{20}$ 1.5394

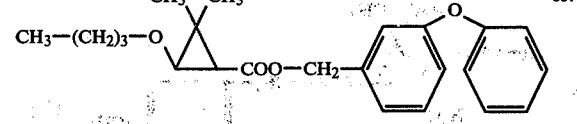

5'-benzyl-3'-furylmethyl 2,2-dimethyl-3-allyloxycyclopropane carboxylate $n_D^{20}$ 1.5463

5'-benzyl-3'-furylmethyl 2,2-dimethyl-3-(1-methyl-n-propoxy)-cyclopropane carboxylate $n_D^{20}$ 1.5542

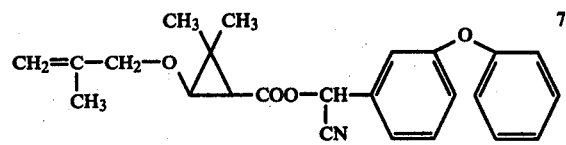

3′-phenoxy-α′-cyanobenzyl 2,2-dimethyl-3-(2-methylallyloxy)-cyclopropane carboxylate $n_D^{20}$ 1.5422

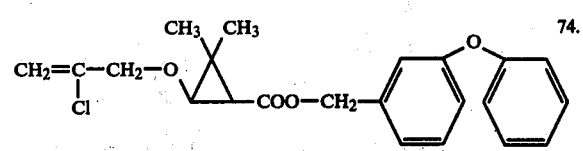

3′-phenoxybenzyl 2,2-dimethyl-3-(2-chloroallyloxy)-cyclopropane carboxylate $n_D^{20}$ 1.5360

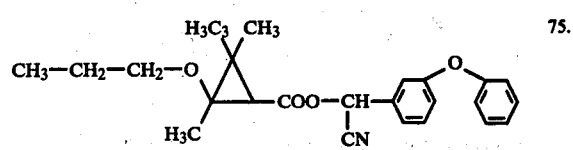

3′-phenoxy-α′-cyanobenzyl 2,2,3-trimethyl-3-n-propoxycyclopropane carboxylate $n_D^{20}$ 1.5377

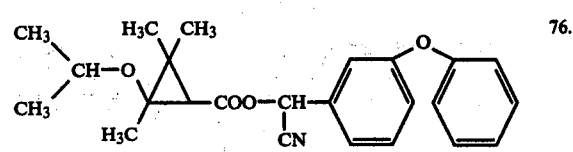

3′-phenoxy-α′-cyanobenzyl 2,2,3-trimethyl-3-i-propoxycyclopropane carboxylate $n_D^{20}$ 1.5422

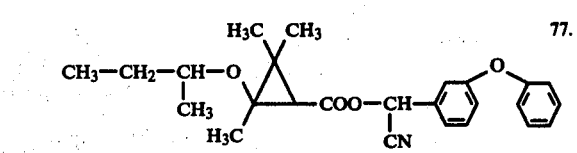

3′-phenoxy-α′-cyanobenzyl 2,2,3-trimethyl-3-(1-methyl-n-propoxy)-cyclopropane carboxylate $n_D^{20}$ 1.5416

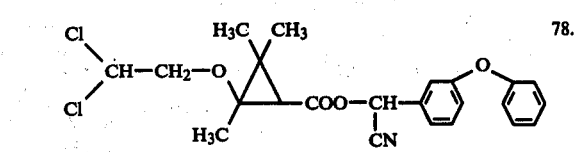

3′-phenoxy-α′-cyanobenzyl 2,2,3-trimethyl-3-(2,2-dichloroethoxy)-cyclopropane carboxylate $n_D^{20}$ 1.5596

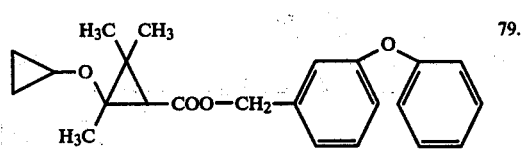

3′-phenoxybenzyl 2,2,3-trimethyl-3-cyclopropoxycyclopropane carboxylate $n_D^{20}$ 1.5327

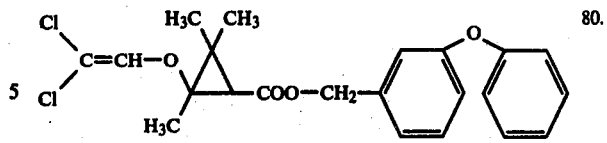

3′-phenoxybenzyl 2,2,3-trimethyl-3-(2,2-dichlorovinyloxy)-cyclopropane carboxylate $n_D^{20}$ 1.5480

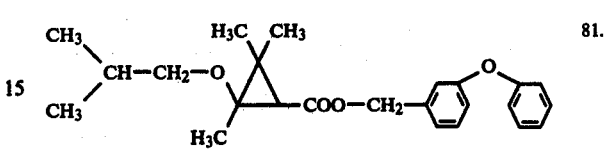

3′-Phenoxybenzyl 2,2,3-trimethyl-3-isobutoxycyclopropane carboxylate $n_D^{20}$ 1.5432

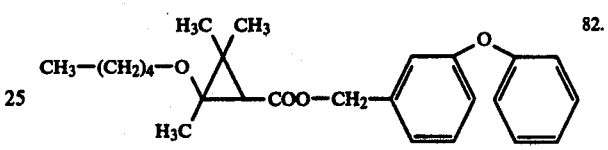

3′-phenoxybenzyl 2,2,3-trimethyl-3-n-amyloxycyclopropane carboxylate $n_D^{20}$ 1.5401

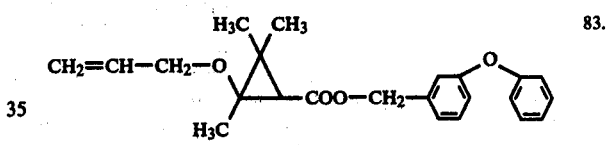

3′-phenoxybenzyl 2,2,3-trimethyl-3-allyloxycyclopropane carboxylate $n_D^{20}$ 1.5305

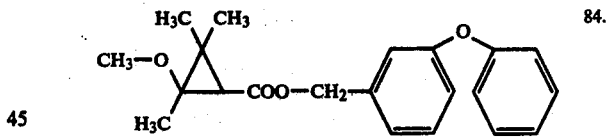

3′-phenoxybenzyl 2,2,3-trimethyl-3-methoxycyclopropane carboxylate $n_D^{20}$ 1.5204

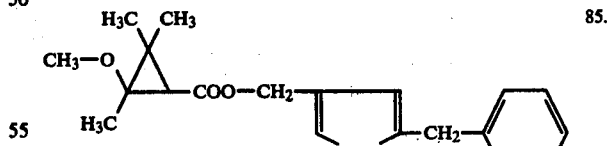

5′-benzyl-3′-furylmethyl 2,2,3-trimethyl-3-methoxycyclopropane carboxylate $n_D^{20}$ 1.5428

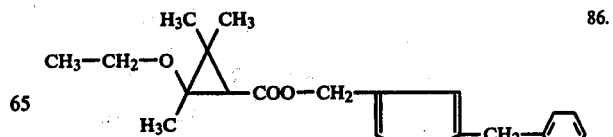

5'-benzyl-3'-furylmethyl 2,2,3-trimethyl-3-ethoxycyclopropane carboxylate $n_D^{20}$ 1.5471

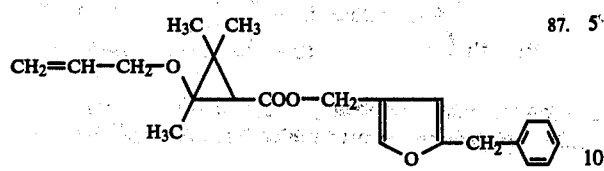

5'-benzyl-3'-furylmethyl 2,2,3-trimethyl-3-allyloxycyclopropane carboxylate $n_D^{20}$ 1.5512

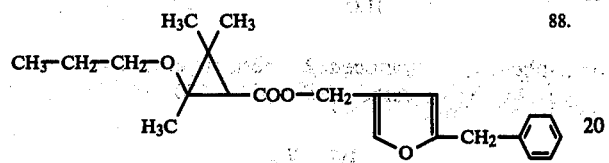

5'-benzyl-3'-furylmethyl 2,2,3-trimethyl-3-n-propoxycyclopropane carboxylate $n_D^{20}$ 1.5519

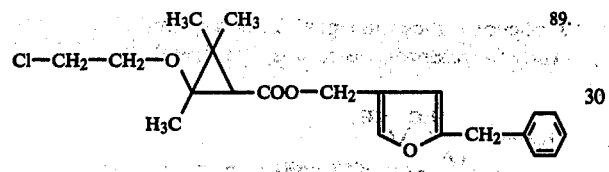

5'-benzyl-3'-furylmethyl 2,2,3-trimethyl-3-(2-chloroethoxy)-cyclopropane carboxylate $n_D^{20}$ 1.5588

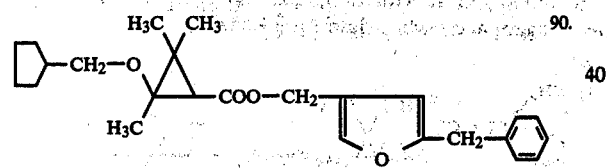

5'-benzyl-3'-furylmethyl 2,2,3-trimethyl-3-cyclopentylmethoxycyclopropane carboxylate $n_D^{20}$ 1.5674

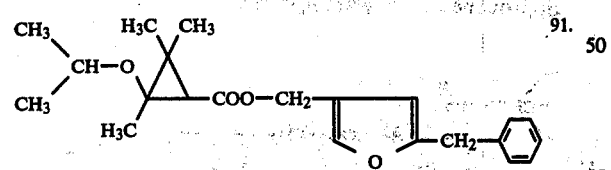

5'-benzyl-3'-furylmethyl 2,2,3-trimethyl-3-isopropoxycyclopropane carboxylate $n_D^{20}$ 1.5492

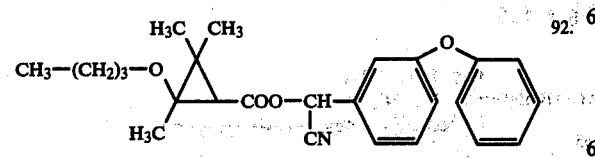

3'-phenoxy-α'-cyanobenzyl 2,2,3-trimethyl-3-n-butoxycyclopropane carboxylate $n_D^{20}$ 1.5503

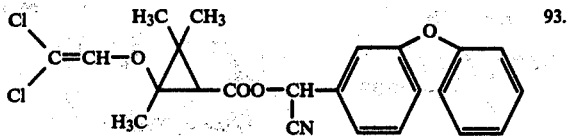

3'-phenoxy-α'-cyanobenzyl 2,2,3-trimethyl-3-(2,2-dichlorovinyloxy)-cyclopropane carboxylate $n_D^{20}$ 1.5617

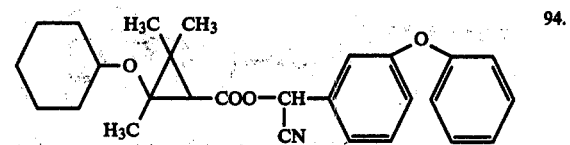

3'-phenoxy-α'-cyanobenzyl 2,2,3-trimethyl-3-cyclohexyloxycyclopropane carboxylate $n_D^{20}$ 1.5568

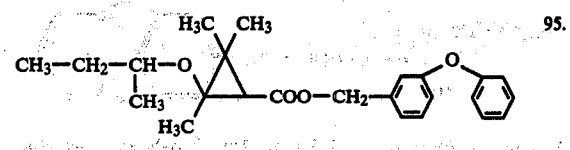

3'-phenoxybenzyl 2,2,3-trimethyl-3-(1-methyl-n-propoxy)-cyclopropan carboxylate $n_D^{20}$ 1.5338

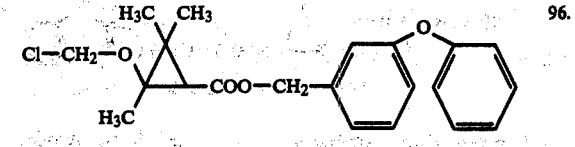

3'-phenoxybenzyl 2,2,3-trimethyl-3-chloromethoxycyclopropane carboxylate $n_D^{20}$ 1.5288

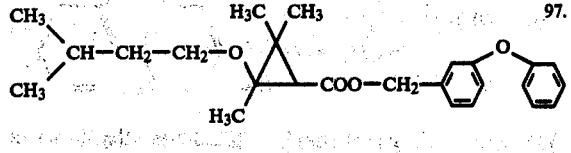

3'-phenoxybenzyl 2,2,3-trimethyl-3-isoamyloxycyclopropane carboxylate $n_D^{20}$ 1.5446

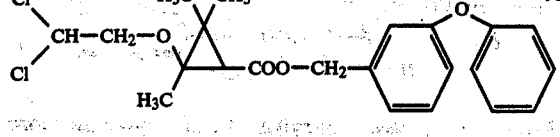

3'-phenoxybenzyl 2,2,3-trimethyl-3-(2,2-dichloroethoxy)-cyclopropane carboxylate $n_D^{20}$ 1.5439

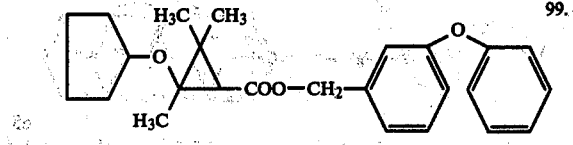

3'-phenoxybenzyl 2,2,3-trimethyl-3-cyclopentyloxycyclopropane carboxylate $n_D^{20}$ 1.5498

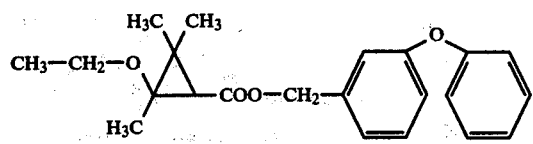

100.

3'-phenoxybenzyl 2,2,3-trimethyl-3-ethoxycyclopropane carboxylate $n_D^{20}$ 1.5264

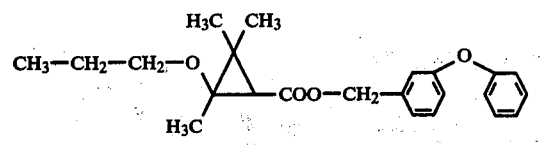

101.

3'-phenoxybenzyl 2,2,3-trimethyl-3-n-propoxycyclopropane carboxylate $n_D^{20}$ 1.5309

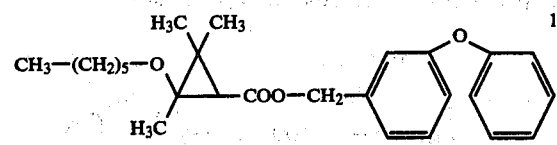

102.

3'-phenoxybenzyl 2,2,3-trimethyl-3-n-hexyloxycyclopropane carboxylate $n_D^{20}$ 1.5427

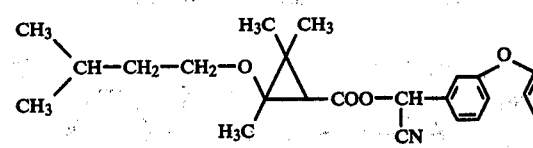

103.

3'-phenoxy-α'-cyanobenzyl 2,2,3-trimethyl-3-isoamyloxycyclopropane carboxylate $n_D^{20}$ 1.5618

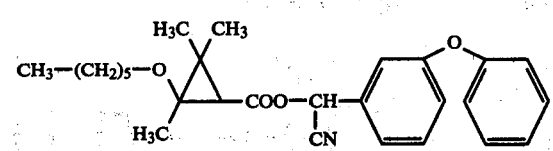

104.

3'-phenoxy-α'-cyanobenzyl 2,2,3-trimethyl-3-n-hexyloxycyclopropane carboxylate $n_D^{20}$ 1.5597

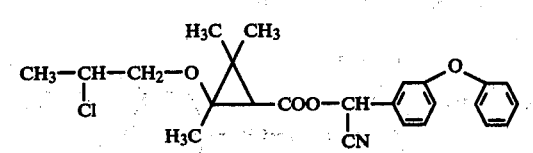

105.

3'-phenoxy-α'-cyanobenzyl 2,2,3-trimethyl-3-(2-chloro-n-propoxy)-cyclopropane carboxylate $n_D^{20}$ 1.5635

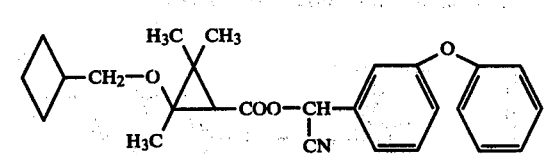

106.

3'-phenoxy-α'-cyanobenzyl 2,2,3-trimethyl-3-cyclobutylmethoxycyclopropane carboxylate $n_D^{20}$ 1.5511

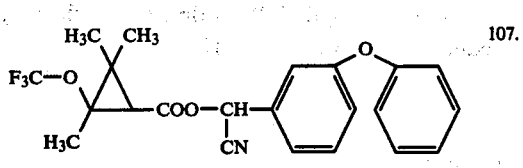

107.

3'-phenoxy-α'-cyanobenzyl 2,2,3-trimethyl-3-trifluoromethoxycyclopropane carboxylate $n_D^{20}$ 1.5418

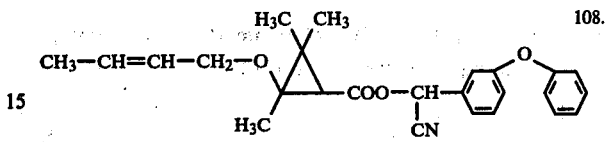

108.

3'-phenoxy-α'-cyanobenzyl 2,2,3-trimethyl-3-crotyloxycyclopropane carboxylate $n_D^{20}$ 1,5580

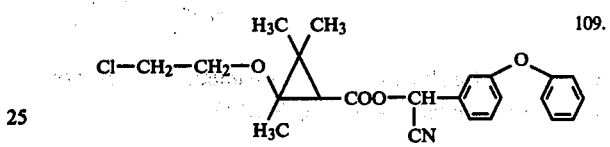

109.

3'-phenoxy-α'-cyanobenzyl 2,2,3-trimethyl-3-(2-chloroethoxy)-cyclopropane carboxylate $n_D^{20}$ 1.5486

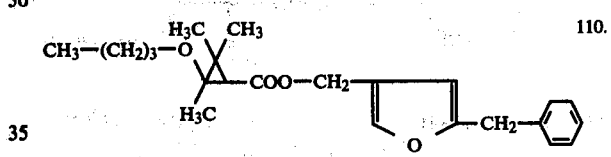

110.

5'-benzyl-3'-furylmethyl 2,2,3-trimethyl-3-n-butoxycyclopropane carboxylate $n_D^{20}$ 1.5584

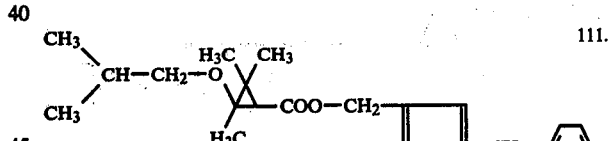

111.

5'-benzyl-3'-furylmethyl 2,2,3-trimethyl-3-isobutoxycyclopropane carboxylate $n_D^{20}$ 1.5571

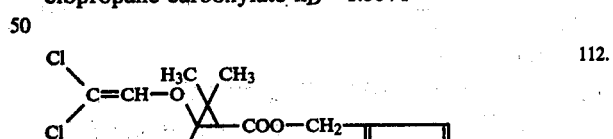

112.

5'-benzyl-3'-furylmethyl 2,2,3-trimethyl-3-(2,2-dichlorovinyloxy)-cyclopropane carboxylate $n_D^{20}$ 1.5628

113.

5'-benzyl-3'-furylmethyl 2,2,3-trimethyl-3-n-amyloxycyclopropane carboxylate $n_D^{20}$ 1.5686

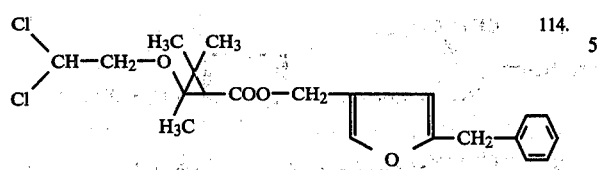
114.

5'-benzyl-3'-furylmethyl 2,2,3-trimethyl-3-(2,2-dichloroethoxy)-cyclopropane carboxylate $n_D^{20}$ 1.5651

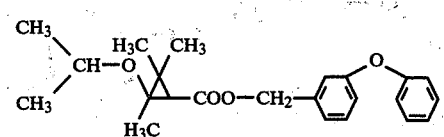
115.

3'-phenoxybenzyl 2,2,3-trimethyl-3-isopropoxycyclopropane carboxylate $n_D^{20}$ 1.5316

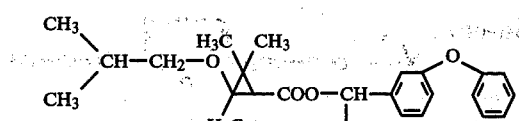
116.

3'-phenoxy-α'-cyanobenzyl 2,2,3-trimethyl-3-isobutoxycyclopropane carboxylate $n_D^{20}$ 1.5492

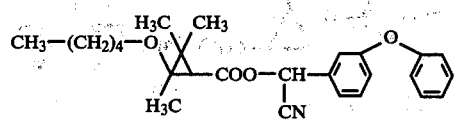
117.

3'-phenoxy-α'-cyanobenzyl 2,2,3-trimethyl-3-n-amyloxycyclopropane carboxylate $n_D^{20}$ 1.5548

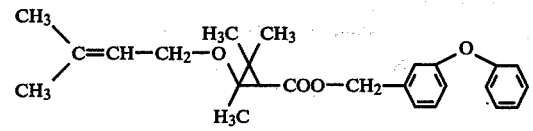
118.

3'-phenoxybenzyl 2,2,3-trimethyl-3-(3-methyl-2-butenyloxy)-cyclopropane carboxylate $n_D^{20}$ 1.5416

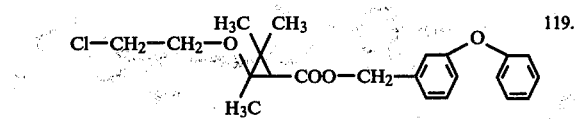
119.

3'-phenoxybenzyl 2,2,3-trimethyl-3-(2-chloroethoxy)-cyclopropane carboxylate $n_D^{20}$ 1.5433

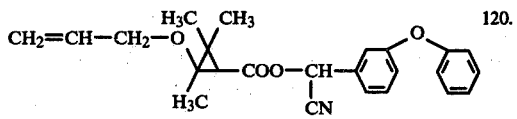
120.

3'-phenoxy-α'-cyanobenzyl 2,2,3-trimethyl-3-allyloxycyclopropane carboxylate $n_D^{20}$ 1.5408

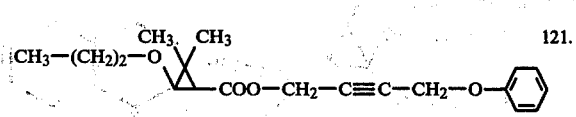
121.

4'-phenoxy-2'-butyne-1'-yl 2,2-dimethyl-3-n-propoxycyclopropane carboxylate $n_D^{20}$ 1.5386

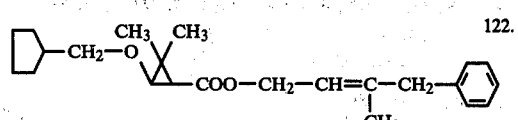
122.

4'-phenyl-3'-methyl-2'-butene-1'-yl 2,2-dimethyl-3-cyclopentylmethoxycyclopropane carboxylate $n_D^{20}$ 1.5529

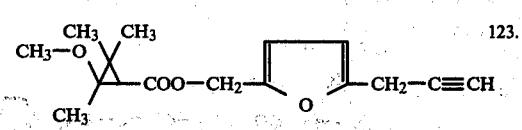
123.

5'-propargyl-2'-furylmethyl 2,2,3-trimethyl-3-methoxycyclopropane carboxylate $n_D^{20}$ 1.5185

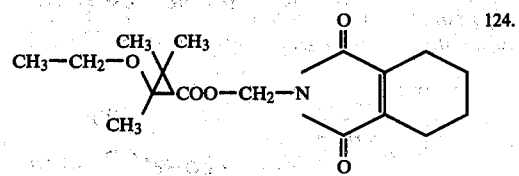
124.

3',4',5',6'-tetrahydrophthalimidemethyl 2,2,3-trimethyl-3-ethoxycyclopropane carboxylate $n_D^{20}$ 1.5390

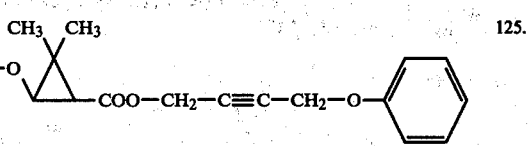
125.

4'-phenoxy-2'-butyne-1'-yl 2,2-dimethyl-3-allyloxycyclopropane carboxylate $n_D^{20}$ 1.5341

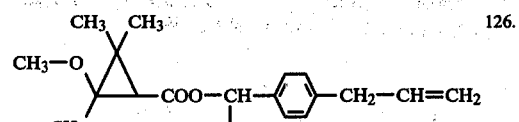
126.

4'-allyl-α'-ethynylbenzyl 2,2,3-trimethyl-3-methoxycyclopropane carboxylate $n_D^{20}$ 1.5376

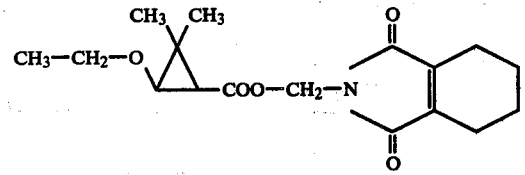

3′,4′,5′,6′-tetrahydrophtalimidemethyl 2,2-dimethyl-3-ethoxycyclopropane carboxylate $n_D^{20}$ 1.5163

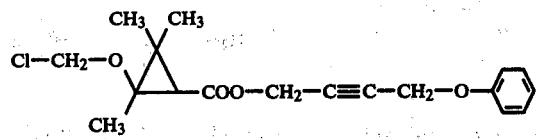

4′-phenoxy-2′-butyne-1′-yl 2,2,3-trimethyl-3-chloromethoxycyclopropane carboxylate $n_D^{20}$ 1.5309

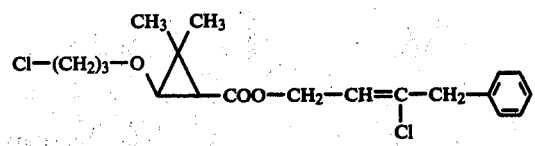

4′-phenyl-3′-chloro-2′-buten-1′-yl 2,2-dimethyl-3-(3-chloro-n-propoxy)-cyclopropane carboxylate $n_D^{20}$ 1.5572

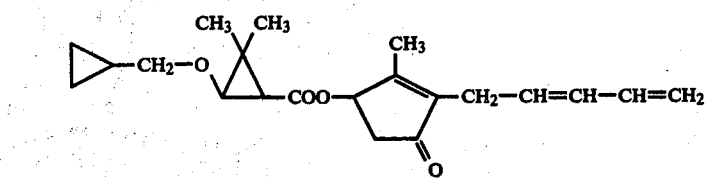

2′-(2,4-pentadienyl)-3′-methyl-2′-cyclopenten-1′-one-4′-yl 2,2-dimethyl-3-cyclopropylmethoxy cyclopropane carboxylate $n_D^{20}$ 1.5540

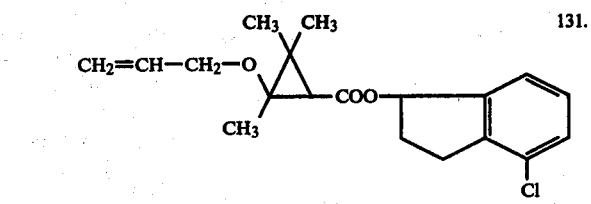

7′-chloro-indane-3′-yl 2,2,3-trimethyl-3-allyloxycyclopropane carboxylate $n_D^{20}$ 1.5539

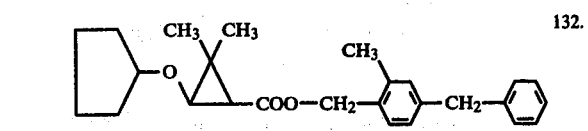

2′-methyl-4′-benzylbenzyl 2,2-dimethyl-3-cyclopentyloxycyclopropane carboxylate $n_D^{20}$ 1.5704

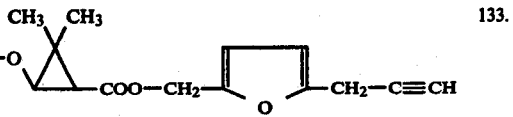

5′-propargyl-2′-furylmethyl 2,2-dimethyl-3-n-butoxycyclopropane carboxylate $n_D^{20}$ 1.5490

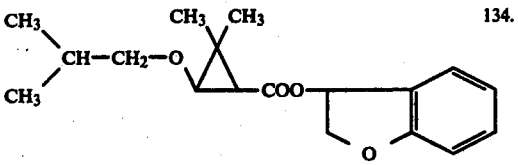

2′,3′-dihydrobenzofuran-3′-yl 2,2-dimethyl-3-isobutoxycyclopropane carboxylate $n_D^{20}$ 1.5417

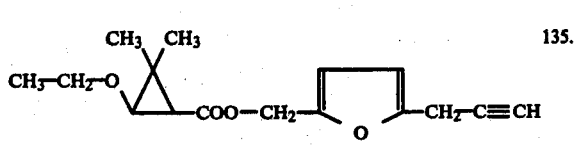

5′-propargyl-2′-furylmethyl 2,2-dimethyl-3-ethoxycyclopropane carboxylate $n_D^{20}$ 1.5375

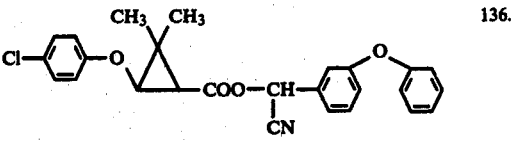

3′-phenoxy-α′-cyanobenzyl 2,2-dimethyl-3-(p-chlorophenoxy)-cyclopropane carboxylate $n_D^{20}$ 1.5856

3′-phenoxy-α′-cyanobenzyl 2,2-dimethyl-3-(p-methylphenoxy)-cyclopropane carboxylate $n_D^{20}$ 1.5817

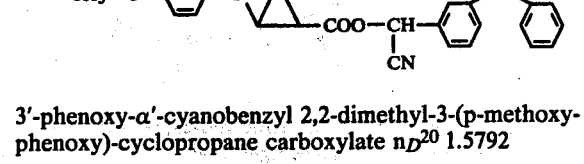

3′-phenoxy-α′-cyanobenzyl 2,2-dimethyl-3-(p-methoxyphenoxy)-cyclopropane carboxylate $n_D^{20}$ 1.5792

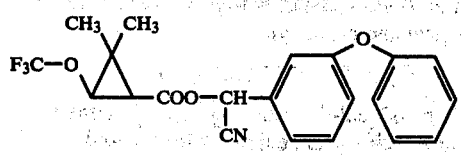

3'-phenoxy-α'-cyanobenzyl 2,2-dimethyl-3-trifluoromethoxycyclopropane carboxylate $n_D^{20}$ 1.5403

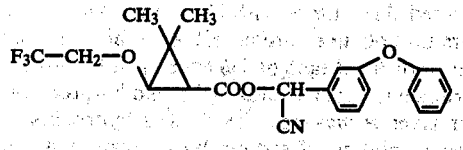

3'-phenoxy-α'-cyanobenzyl 2,2-dimethyl-3-(2,2,2-trifluoroethoxy)-cyclopropane carboxylate $n_D^{20}$ 1.5487

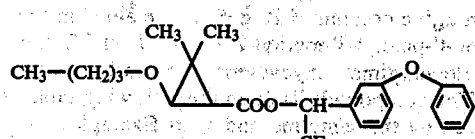

3'-phenoxy-α'-trifluoromethylbenzyl 2,2-dimethyl-3-n-butoxycyclopropane carboxylate $n_D^{20}$ 1.5390

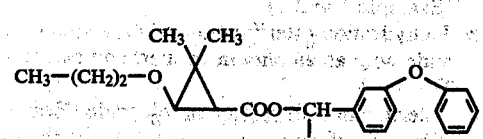

3'-phenoxy-α'-ethynylbenzyl 2,2-dimethyl-3-n-propoxycyclopropane carboxylate $n_D^{20}$ 1.5304

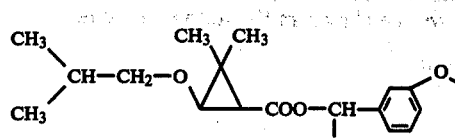

3'-phenoxy-α'-trifluoromethylbenzyl 2,2-dimethyl-3-isobutoxycyclopropane carboxylate $n_D^{20}$ 1.5382

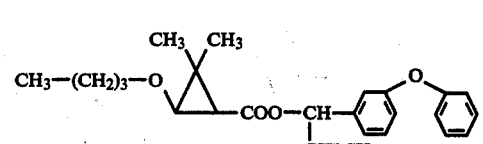

3'-phenoxy-α'-ethynylbenzyl 2,2-dimethyl-3-n-butoxycyclopropane carboxylate $n_D^{20}$ 1.5375

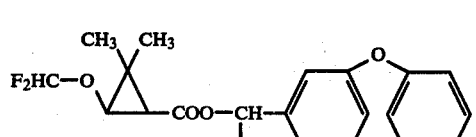

3'-phenoxy-α'-cyanobenzyl 2,2-dimethyl-3-difluoromethoxycyclopropane carboxylate $n_D^{20}$ 1.5454

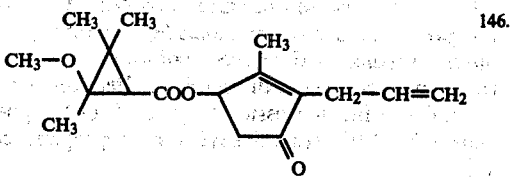

2'-allyl-3'-methyl-2'-cyclopenten-1'-one-4'-yl 2,2,3-trimethyl-3-methoxycyclopropane carboxylate $n_D^{20}$ 1.5380

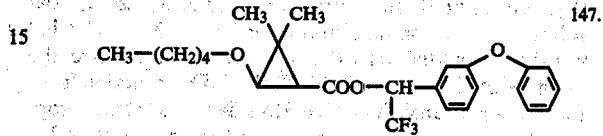

3'-phenoxy-α'-trifluoromethylbenzyl 2,2-dimethyl-3-n-amyloxycyclopropane carboxylate $n_D^{20}$ 1.5469

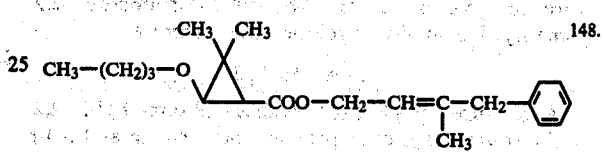

4'-phenyl-3'-methyl-2'-buten-1'-yl 2,2-dimethyl-3-n-butoxycyclopropane carboxylate $n_D^{20}$ 1.5447

The process for producing the esters of the present invention will be explained in more detail referring to the synthesis Examples.

EXAMPLE 1

5.1 g of 3-phenoxy-α-cyanobenzyl chloride is added into a solution of 3.9 g of 2,2-dimethyl-3-cyclobutoxycyclopropane carboxylic acid dissolved in 50 ml of dimethylformamide, to which 4 ml of triethylamine is added with stirring. The reaction is carried out at 60°–80° C. for 3 hours. The reaction mixture is dissolved in ether and the ether solution is fully washed with diluted hydrochloric acid, aqueous solution of sodium bicarbonate and aqueous solution of sodium chloride in order. It is dried over sodium sulfate and thereafter ether is distilled off under reduced pressure to give 6.8 g of 3'-phenoxy-α'-cyanobenzyl 2,2-dimethyl-3-cyclobutoxycyclopropane carboxylate.

EXAMPLE 2

3.1 g of 2,2-dimethyl-3-ethoxycyclopropane carboxylic acid and 3.7 g of 3,4,5,6-tetrahydrophthalimide methylol are added into 50 ml of dried benzen and 6.2 g of dicyclohexyl carbodiimide is added into the solution. The solution is allowed to stand in a tightly stoppered vessel for one night. The next day, the reaction is completed by heating under reflux for 4 hours. After cooling, precipitated dicyclohexylurea is filtered off. Oily substance obtained by condensing the filtrate is purified through a column of silica gel to obtain 4.5 g of 3',4',5',6'-tetrahydrophthalimidemethyl 2,2-dimethyl-3-ethoxycyclopropane carboxylate.

EXAMPLE 3

4.1 g of sodium 2,2,3-trimethyl-3-allyloxycyclopropane carboxylate and 4.5 g of 3-phenoxybenzylchloride are dissolved into 50 ml of benzene. After reaction is carried out under reflux under a stream of nitrogen for 3 hours, the reaction mixture is cooled. After filtering the precipitated sodium chloride, the filtrate is thoroughly washed with aqueous solution of sodium chloride and dried over sodium sulfate. Benzene is distilled off under reduced pressure to give 6.8 g of 3'-phenoxybenzyl 2,2,3-trimethyl-3-allyloxycyclopropane carboxylate.

EXAMPLE 4

4.4 g of 2,2-dimethyl-3-n-amyloxycyclopropane carboxylate acid chloride is dissolved in 15 ml of dried benzene and a solution of 3.7 g of 5-benzyl-3-furylmethylalcohol in 20 ml of dried benzene is added into the solution. As a condensation accelerator, 3 ml of dried pyridine is added into the solution to precipitate the crystals of pyridine hydrochloride. The reaction mixture thus prepared is allowed to stand in a tightly stoppered vessel at room temperature for one night. After the crystals of pyridine hydrochloride are filtered off, the benzene solution is dried over sodium sulfate. Thereafter benzene is distilled off under reduced pressure to give 6.8 g of 5'-benzyl-3'-furylmethyl 2,2-dimethyl-3-n-amyloxycyclopropane carboxylate.

EXAMPLE 5

A mixture of 4.8 g of methyl 2,2-dimethyl-3-(2,2-dichlorovinyloxy)-cyclopropane carboxylate and 3.3 g of 7-methyl-2,3-dihydrobenzofuran-3-ol is heated up to 150° C. When the temperature reaches at 150° C., 0.25 g of sodium is added to the heated solution and methanol is started distilling off. When distillation of methanol ceases, another 0.25 g of sodium is added into the solution. The above-mentioned operation is repeated while keeping the temperature at about 150° C. until theoretical quantity of methanol is obtained. Then, the mixture is cooled and dissolved in ether. The ether solution is washed with diluted hydrochloric acid, aqueous solution of sodium bicarbonate and aqueous solution of sodium chloride one after another and dried over sodium sulfate. Ether is distilled off under a reduced pressure to give 6.2 g of 7'-methyl-2',3'-dihydrobenzofuran-3'-yl 2,2-dimethyl-3-(2,2-dichlorovinyloxy)-cyclopropane carboxylate.

EXAMPLE 6

8.2 g of 2,2-dimethyl-3-cyclopentylmethoxycyclopropane carboxylic acid anhydride and 3.2 g of 4-phenyl-3-methyl-2-butene-1-ol are dissolved in 50 ml of dried pyridine and the solution is kept stirring at room temperature for one night. Next day, the reaction solution is poured into 100 g of ice water and the mixture is extracted three times with 20 ml of ether. Three ether layers thus obtained are combined, which are extracted twice with 30 ml each of 5% aqueous solution of sodium hydroxide to remove carboxylic acid by-produced. The ether layer is washed with diluted hydrochloric acid, aqueous solution of sodium bicarbonate and saturated solution of sodium chloride in order, and thereafter is dried over sodium sulfate. Ether is removed under reduced pressure to give a crude ester, which is purified through a column of 20 g of active alumina to give 6.0 g of 4'-phenyl-3'-methyl-2'-butene-1'-yl 2,2-dimethyl-3-cyclopentylmethoxycyclopropane carboxylate.

The compounds listed in the following table are prepared by the same method as in Examples 1-6. In the table 1, a, b, c, d, e in column of esterification method mean as follows:

a. Esterification of salt of alkali metal, silver or organic tertiary base of acid with halide of alcohol. (Example 1 and 3)
b. Dehydration-esterification of dicyclohexylcarboimide with an alcohol in an inert solvent. (Example 2)
c. Esterification through acid chloride (Example 4)
d. Transesterification in the presence of the catalyst of alkali metal, alkali metal alkoxide or sodium hydride. (Example 5)
e. Esterification through acid anhydride. (Example 6)

The representative compounds of the present invention will be shown in the following table.

TABLE 1

| Compound No. | R$_2$—O—C(CH$_3$)(CH$_3$)—R$_1$ (R$_2$O, R$_1$) | R$_3$ | Esterification Method | Yield (%) | | C | H | N | Ultimate analysis value |
|---|---|---|---|---|---|---|---|---|---|
| 1. | CH$_3$—CH(CH$_3$)—CH(CH$_3$)—O— | —CH(CN)—C$_6$H$_4$—O—C$_6$H$_5$ | b | 82 | A: B: | 71.43, 71.79 | 5.80, 5.98 | 4.02, 3.99 | C$_{21}$H$_{21}$NO$_4$ |
| 2. | CH$_3$—CH(CH$_3$)—CH—CH$_2$—O— | —CH(CN)—C$_6$H$_4$—O—C$_6$H$_5$ | a | 86 | A: B: | 73.41, 73.28 | 6.82, 6.87 | 3.50, 3.56 | C$_{24}$H$_{27}$NO$_4$ |
| 3. | CH$_3$—O—C(CH$_3$)(CH$_3$)— | —CH(CN)—C$_6$H$_4$—O—C$_6$H$_5$ | c | 67 | A: B: | 72.36, 72.33 | 6.27, 6.30 | 3.85, 3.84 | C$_{22}$H$_{23}$NO$_4$ |
| 4. | CH$_3$—CH$_2$—O—C(CH$_3$)— | —CH(CN)—C$_6$H$_4$—O—C$_6$H$_5$ | a | 74 | A: B: | 72.67, 72.82 | 6.58, 6.60 | 3.70, 3.69 | C$_{23}$H$_{25}$NO$_4$ |
| 5. | CH$_3$—CH$_2$—O— | —CH(CN)—C$_6$H$_4$—O—C$_6$H$_5$ | b | 81 | A: B: | 72.50, 72.33 | 6.32, 6.30 | 3.87, 3.84 | C$_{22}$H$_{23}$NO$_4$ |
| 6. | CH$_3$—(CH$_2$)$_2$—O— | —CH$_2$—C$_6$H$_4$—O—C$_6$H$_5$ | a | 90 | A: B: | 74.29, 74.58 | 7.38, 7.34 | —, — | C$_{22}$H$_{26}$O$_4$ |
| 7. | CH$_3$—(CH$_2$)$_3$—O— | —CH(CN)—C$_6$H$_4$—O—C$_6$H$_5$ | b | 82 | A: B: | 73.16, 73.28 | 6.88, 6.87 | 3.58, 3.56 | C$_{24}$H$_{27}$NO$_4$ |

TABLE 1-continued

| Compound No. | R₁ | R₃ | Esterification Method | Yield (%) | | Ultimate analysis value C, H, N, | | | |
|---|---|---|---|---|---|---|---|---|---|
| 9. | CH₃—(CH₂)₄—O— (with gem-dimethyl cyclopropyl) | —CH(C₆H₄OC₆H₄CN) | e | 71 | A:<br>B: | 73.65,<br>73.71, | 7.14,<br>7.13, | 3.46<br>3.44 | C₂₅H₂₉NO₄ |
| 11. | CH₃—(CH₂)₃—O— (with gem-dimethyl cyclopropyl) | —CH₂-(2,5-dihydrofuran-2-yl)-phenyl | d | 73 | A:<br>B: | 74.19,<br>74.16, | 7.85,<br>7.87, | —<br>— | C₂₂H₂₈O₄ |
| 12. | (CH₃)₂CHCH₂—O— (with gem-dimethyl cyclopropyl) | —CH₂-(2,5-dihydrofuran-2-yl)-phenyl | c | 70 | A:<br>B: | 74.10,<br>74.16, | 7.89,<br>7.87, | —<br>— | C₂₂H₂₈O₄ |
| 14. | CH₃—(CH₂)₄—O— (with gem-dimethyl cyclopropyl) | —CH₂-(5-ethynyl-2,5-dihydrofuran-2-yl) | e | 76 | A:<br>B: | 71.76,<br>71.70, | 8.14,<br>8.18, | —<br>— | C₁₉H₂₆O₄ |
| 15. | CH₃—(CH₂)₄—O— (with gem-dimethyl cyclopropyl) | —CH₂-(allyl-methyl-cyclopentenone) | c | 68 | A:<br>B: | 71.81,<br>71.86, | 8.99,<br>8.98, | —<br>— | C₂₀H₃₀O₄ |
| 16. | CH₃—(CH₂)₂—O— (with gem-dimethyl cyclopropyl) | —CH₂-(2-methylphenoxymethyl) | b | 80 | A:<br>B: | 72.22,<br>72.29, | 8.47,<br>8.43, | —<br>— | C₂₀H₂₈O₄ |

TABLE 1-continued

| Compound No. | $R_2-O \diagdown \diagup CH_3 \; CH_3 \diagdown \diagup R_1$ | $R_3$ | Esterification Method | Yield (%) | | Ultimate analysis value C, H, N, | | | |
|---|---|---|---|---|---|---|---|---|---|
| 17. | $CH_3-(CH_2)_2-O-$ | (2-oxo-cyclohexenyl with -CH₂-N-) | d | 72 | A:<br>B: | 64.53,<br>64.48, | 7.42,<br>7.46, | 4.16<br>4.18 | $C_{18}H_{25}NO_5$ |
| 18. | $CH_3\diagdown CH-CH_2-O-$ $CH_3\diagup$ | (CCl₂=CH-O-phenyl-CH₂-CN) | a | 81 | A:<br>B: | 58.19,<br>58.25, | 5.60,<br>5.58, | 3.36<br>3.40 | $C_{20}H_{23}NO_4Cl$ |
| 24. | $CH_3-(CH_2)_4-O-$ | $-CH_2-CH=C\diagdown \diagup phenyl \; Cl$ | c | 74 | A:<br>B: | 69.19,<br>69.14, | 7.93,<br>7.96, | —<br>— | $C_{21}H_{29}O_3Cl$ |
| 25. | $CH_3-(CH_2)_3-O-$ | (methylbenzofuranyl-CH₂-) | e | 77 | A:<br>B: | 71.76,<br>71.70, | 8.16,<br>8.18, | —<br>— | $C_{19}H_{26}O_4$ |
| 27. | $CH_3-(CH_2)_2-O-$ | $-CH_2-C\equiv CH$ (furyl) | b | 75 | A:<br>B: | 70.19,<br>70.34, | 7.63,<br>7.59, | —<br>— | $C_{17}H_{22}O_4$ |
| 28. | $CH_3\diagdown CH-CH_2-O-$ $CH_3\diagup$ | $CH_2-CH=CH_2$ (cyclopentenone with -CH₂-) | d | 76 | A:<br>B: | 71.30,<br>71.25, | 8.70,<br>8.75, | —<br>— | $C_{19}H_{28}O_4$ |

TABLE 1-continued

| Compound No. | R₁ | R₃ | Esterification Method | Yield (%) | | Ultimate analysis value | | | |
|---|---|---|---|---|---|---|---|---|---|
| | $R_2-O \overset{CH_3\ CH_3}{\underset{R_1}{\triangle}}$ | | | | | C, | H, | N, | |
| 29. | $CH_3-(CH_2)_3-O-$ | 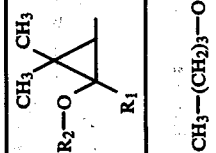 | c | 68 | A:<br>B: | 65.38,<br>65.33, | 7.70,<br>7.74, | 4.02,<br>4.01 | $C_{19}H_{27}NO_5$ |
| 31. | 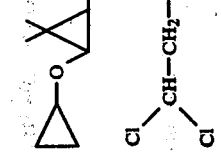 | 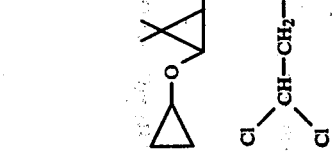 | d | 70 | A:<br>B: | 71.55,<br>71.52, | 7.25,<br>7.28, | —<br>— | $C_{18}H_{22}O_4$ |
| 34. | 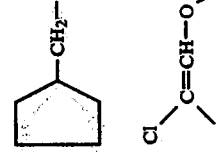 | 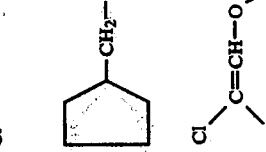 | b | 79 | A:<br>B: | 61.07,<br>61.11, | 4.86,<br>4.84, | 3.24<br>3.23 | $C_{22}H_{21}NO_4Cl_2$ |
| 41. | 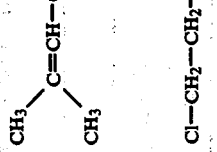 | 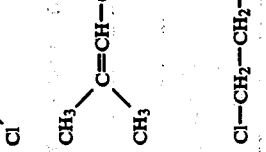 | a | 78 | A:<br>B: | 76.09,<br>76.14, | 7.63,<br>7.61, | —<br>— | $C_{25}H_{30}O_4$ |
| 52. | $\underset{Cl}{\overset{Cl}{\diagdown}}C=CH-O-$ |  | b | 76 | A:<br>B: | 60.71,<br>60.76, | 5.10,<br>5.06, | —<br>— | $C_{20}H_{20}O_4Cl_2$ |
| 61. | $CH_3-\underset{CH_3}{\overset{|}{C}}-CH=CH-CH_2-O-$ |  | a | 81 | A:<br>B: | 74.10,<br>74.07, | 6.64,<br>6.67, | 3.44<br>3.46 | $C_{25}H_{27}NO_4$ |
| 89. | $Cl-CH_2-CH_2-CH_2-O-\underset{CH_3}{|}$ |  | e | 72 | A:<br>B: | 66.90,<br>66.93, | 6.66,<br>6.64, | —<br>— | $C_{21}H_{25}O_4Cl$ |

TABLE 1-continued

| Compound No. | R₃ | $R_2-O\begin{matrix}CH_3\ CH_3\\ \diagdown/\\ \diagup\diagdown\\ R_1\end{matrix}$ | Esterification Method | Yield (%) | | Ultimate analysis value C, H, N, | | | |
|---|---|---|---|---|---|---|---|---|---|
| 94. | -CH(CN)-C₆H₄-O-C₆H₅ (m-phenoxy-α-cyanobenzyl) | R₁ = cyclohexyl, R₂ = CH₃ | c | 69 | A:<br>B: | 74.70,<br>74.83, | 7.20,<br>7.16, | 3.24,<br>3.23 | C₂₇H₃₁NO₄ |
| 121. | -CH₂-C≡C-CH₂-O-C₆H₅ | R₁ = CH₃, R₂ = CH₃-(CH₂)₂- | d | 65 | A:<br>B: | 72.11,<br>72.15, | 7.63,<br>7.59, | —<br>— | C₁₉H₂₄O₄ |
| 126. | -CH₂-C₆H₄-C≡CH (p-ethynylbenzyl) | R₁ = CH₃, R₂ = CH₃- | b | 74 | A:<br>B: | 76.88,<br>76.92, | 7.71,<br>7.69, | —<br>— | C₂₀H₂₄O₃ |
| 129. | -CH₂-CH=C(Cl)-CH₂-C₆H₅ | R₁ = CH₃, R₂ = Cl-(CH₂)₃- | a | 78 | A:<br>B: | 61.42,<br>61.46, | 6.49,<br>6.47, | —<br>— | C₁₉H₂₄O₃Cl₂ |
| 130. | 2-methyl-3-(2-propenyl)-4-oxo-2-cyclopentenyl-allyl | R₁ = CH₃, R₂ = cyclopropyl-CH₂- | a | 83 | A:<br>B: | 73.29,<br>73.26, | 8.13,<br>8.14, | —<br>— | C₂₁H₂₈O₄ |
| 131. | 8-chloro-2,3-dihydro-1H-indene | R₁ = CH₃, R₂ = CH₂=CH-CH₂- | c | 67 | A:<br>B: | 68.22,<br>68.16, | 6.85,<br>6.88, | —<br>— | C₁₉H₂₃O₃Cl |

TABLE 1-continued

| Compound No. | R3 | Esterification Method | Yield (%) | | Ultimate analysis value | | | |
|---|---|---|---|---|---|---|---|---|
| | | | | | C, | H, | N, | |
| 132. | CH₃—O—R₁ with CH₃ CH₃ and —CH₂— attached to phenyl ring bearing CH₃, with —CH₂—O—cyclopentyl | a | 82 | A:<br>B: | 79.46,<br>79.59, | 8.19,<br>8.16, | —<br>— | C₂₆H₃₂O₃ |

Note:
A: Experimental result
B: Calculated value 2,2-dimethyl-3-alkoxycyclopropane carboxylic acid and 2,2,3-trimethyl-3-alkoxycyclopropane carboxylic acid constituting the compounds of the present invention can be easily prepared by using the ethers produced by the methods described in Bull. Soc. Chim., France, 1966 (2), 734 and J. Chem. Soc., 5225 (1965) and the substituted acrylates produced by the method described in Arch. Pharm. 287, 129 (1954) as starting material, for instance, as shown in Steps 1 and 2.

Step 1:

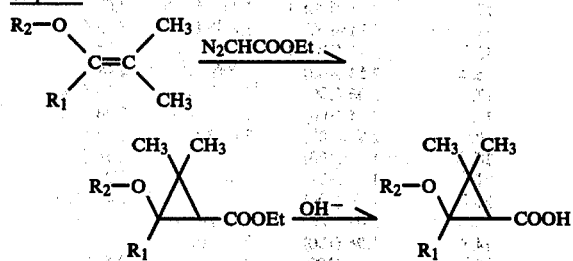

Step 2:

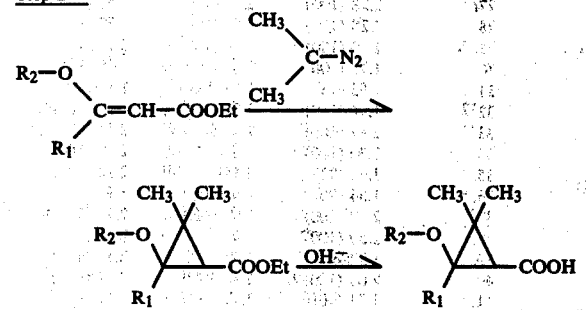

EXAMPLE 7

28 g of n-amyl-1-isobutenyl ether and 1 g of copper sulfate are placed in a 300 ml three necked flask and then 0.5 g of ethyl diazoacetate is added thereto. The mixture is heated at about 120° C. and when nitrogen gas is continuously generated and the reaction starts, 11 g of ethyl diazoacetate is gradually dropped into the reaction mixture while keeping temperature at around 120° C. After the reaction is completed, the reaction mixture is filtered and the filtrate is distilled under reduced pressure to give 16.5 g of ethyl 2,2-dimethyl-3-n-amyloxycyclopropane carboxylate (b.p. 133°–137° C./20 mmHg). 100 ml of 2 N methanol solution of sodium hydroxide is added into the reaction product, which is heated under reflux for 30 minutes. Subsequently, methanol is removed under reduced pressure and water is added into the mixture. Adding concentrated hydrochloric acid, the mixture is made acidic and then extracted three times with 50 ml of chloroform.

The three chloroform layers are combined and dried over anhydrous sodium sulfate. Then chloroform is distilled off under reduced pressure to give 14.5 g of 2,2-dimethyl-3-n-amyloxycyclopropane carboxylic acid.

EXAMPLE 8

A newly prepared ether solution of about 7 g of dimethyl diazomethane is cooled to $-50°\sim -70°$ C. with dry ice-acetone. A solution of 15.0 g of ethyl 3-methoxycrotonate dissolved in 100 ml of ether is dropped gradually into the cooled ether solution. After finished dropping, the reaction liquid is kept at this temperature for three hours and then is allowed to stand at room temperature until the colour of dimethyldiazomethane disappears. Thereafter ether is distilled off to give 20 g of the oily matter of 4-methoxy-4,5,5-trimethyl-1-pyrazoline-3-carboxylate. The pyrazoline ester is gradually heated up to 140° C. under reflux and it is kept at 160° C. for 30 minutes after creasing the boiling. After cooling, water is added into the reaction mixture and the mixture is extracted with ether. Ether is distilled off under reduced pressure to yield 16.2 g of ethyl 2,2,3-trimethyl-3-methoxycyclopropane carboxylic acid (b.p. 122°–126° C./20 mmHg). The product is dissolved in 100 ml of methanol and 20 ml of 40% aqueous solution of sodium hydroxide is added into the solution. The solution is heated under reflux for 1 hour. Methanol is distilled off under reduced pressure and the residue is diluted with 60 ml of water, acidified with hydrochloric acid and extracted three times with 50 ml each of chloroform. The chloroform layers are combined, which is dried over anhydrous sodium sulfate and chloroform is distilled off under reduced pressure to give 14.5 g of 2,2,3-trimethyl-3-methoxycyclopropane carboxylic acid.

The compounds of the present invention which are novel one are solid or liquid at room temperature and usually easily soluble in organic solvent. Accordingly, they may be used as ingredients in insecticidal sprays in the form of emulsion, solution, powder, wettable powder and aerosol, etc. In addition, they may be used as insecticides for fumigation by mixing them with some appropriate substrate such as powdered wood and making mosquito incense sticks. Furthermore, these compounds show also strong effect as mosquito incense sticks when they are employed as insecticides for heating and evaporating use. Namely, they are dissolved in a suitable organic solvent and the solution is absorbed into a carrier and then the resulting product is heated on an appropriate heater. The compounds of the present invention are more stable to light than the conventional chrysanthemum monocarboxylate and they have wide insecticidal spectrum and exhibit excellent effect against the insect pests which is now resistant to organic phosphorous insecticides and carbamate insecticides. In addition as they are low toxic and at low cost, they may be used as agricultural insecticides which are replaceable with conventionally used the organic phosphorous insecticides and the organic chlorine insecticides.

Addition of some synergists into the compounds, for example, N-octylbicycloheptene dicarboxyimide (MGK-264 is the commercial name), a mixture composed of N-octylbicycloheptene dicarboxyimide and arylsulfonic acid salt (MGK-5026 is the commercial name), n-octyl-1-isopropyl-4-methylbicyclo-[2,2,2,]oct-5-en-2,3-dicarboxyimide, octachlorodipropylether, or piperonylbutoxide, can enhance the insecticidal effect.

The compositions for various purposes can be prepared by mixing the compounds of the present invention with other insecticides, say, the organic phosphorous insecticide such as fenitrothion, DDVP(dichlorvos) and diazinon; carbamate insecticide such as 1-naphthyl-N-methylcarbamate, 3,4-dimethyl phenyl-N-methylcarbamate; conventionally used pyrethroid insecticides such as pyrethrin, allethrin, phthalthrin, furamethrin, phenothrin, permethrin, cypermethrin, decamethrin, fenvalerate and fenpropanate; the insecticides such as cartap, chlorphenamidine, methomyl or acaricide miticide, germicide, nematocide, herbicide, plant growth regulator, fertilizer and other agrochemicals.

Therefore reduction of labor and the synergistic effects, for example excellent effect against pests which are resistant to the organic phosphorus and carbamate insecticide, can be highly expected. In order to show the excellent effect of the compounds of the present invention, the test results on light stability and insecticidal effect of the compounds are given in the following.

TEST EXAMPLE 1

About 50 mg each of 10 compounds selected from the above-shown compounds of the present invention and conventionally used pyrethroid is thinly spread on the bottom of a glass vessel having a diameter of 3 cm. Each compound in the vessel is exposed to sun light outdoors on a sunny day in summer from 9 A.M. to 5 P.M. After a given period of time elapsed, each compound is taken into a vessel with 50 ml of acetone and concentrated. Residual ratio (%) of the compounds is determined by means of a gas chromatography. The numbers of the tested compounds correspond to those of the compounds of the formula (I) mentioned above.

TABLE 2

|  | One day Exposure | Two day Exposure | Three day Exposure | Four day Exposure | Five day Exposure |
|---|---|---|---|---|---|
| Allethrin | 43 | 22 | 4 | — | — |
| Resmethrin | 88 | 40 | 8 | — | — |
| Phenothrin | 92 | 72 | 54 | 27 | 5 |
| 2. | 95 | 94 | 88 | 82 | 75 |
| 4. | 92 | 86 | 81 | 79 | 73 |
| 8. | 93 | 89 | 80 | 74 | 70 |
| 13. | 92 | 87 | 79 | 68 | 50 |
| 16. | 94 | 89 | 82 | 77 | 69 |
| 18. | 95 | 88 | 83 | 79 | 71 |
| 24. | 95 | 88 | 80 | 75 | 58 |
| 28. | 93 | 85 | 76 | 57 | 34 |
| 47. | 97 | 93 | 86 | 82 | 76 |
| 132. | 96 | 90 | 84 | 80 | 75 |

As is obvious from the above results, the compounds of the present invention are far more stable against sun light than conventionally used pyrethroid. This means that when the compounds of the present invention are used outdoors, they are expected to exhibit an excellent and persistent effect.

TEST EXAMPLE 2

Insecticidal effect by spraying test

With respect to each 0.2% kerosene solution of 148 compounds of the present invention which are exemplified above (A), a kerosene solution containing 0.2% of each compound of the present invention and 0.8% of piperonylbutoxide (B), a kerosene solution containing 0.1% of each compound of the present invention and 0.1% of phthalthrin (C), a 0.2% kerosene solution of allethrin and a 0.2% kerosene solution of phthalthrin, the relative effect values are estimated from the knockdown rate of house flies by spraying and the mortality after 24 hours is obtained as follows:

TABLE 3

| Compound | (A) | (B) | (C) |
|---|---|---|---|
| Allethrin | 1.00 (26) | — | — |
| Phthalthrin | 2.15 (34) | — | — |
| 1. | 1.58 (100) | 1.84 (100) | 1.79 (100) |
| 2. | 1.70 (100) | 1.92 (100) | 1.93 (100) |

TABLE 3-continued

| Compound | (A) | (B) | (C) |
|---|---|---|---|
| 3. | 1.41 (95) | 1.75 (100) | 1.82 (98) |
| 4. | 1.92 (100) | 2.24 (100) | 2.18 (100) |
| 5. | 1.74 (100) | 1.95 (100) | 1.96 (100) |
| 6. | 2.09 (100) | 2.70 (100) | 2.51 (100) |
| 7. | 1.81 (100) | 2.32 (100) | 2.10 (100) |
| 8. | 1.85 (100) | 2.17 (100) | 2.04 (100) |
| 9. | 1.97 (100) | 2.36 (100) | 2.12 (100) |
| 10. | 1.83 (100) | 2.29 (100) | 2.04 (100) |
| 11. | 2.54 (100) | 3.03 (100) | 2.84 (100) |
| 12. | 2.51 (100) | 2.95 (100) | 2.74 (100) |
| 13. | 3.28 (100) | 3.84 (100) | 3.02 (100) |
| 14. | 2.91 (100) | 3.48 (100) | 3.15 (100) |
| 15. | 2.75 (100) | 3.26 (100) | 2.94 (100) |
| 16. | 2.54 (100) | 2.90 (100) | 2.69 (100) |
| 17. | 3.06 (100) | 3.72 (100) | 3.16 (100) |
| 18. | 2.14 (100) | 2.53 (100) | 2.24 (100) |
| 19. | 2.28 (100) | 2.64 (100) | 2.37 (100) |
| 20. | 1.82 (100) | 2.29 (100) | 2.18 (100) |
| 21. | 1.33 (80) | 1.83 (98) | 1.86 (85) |
| 22. | 2.16 (100) | 2.57 (100) | 2.48 (100) |
| 23. | 2.05 (100) | 2.65 (100) | 2.36 (100) |
| 24. | 1.96 (100) | 2.25 (100) | 2.17 (100) |
| 25. | 2.32 (100) | 2.77 (100) | 2.58 (100) |
| 26. | 2.09 (100) | 2.49 (100) | 2.50 (100) |
| 27. | 2.28 (100) | 2.61 (100) | 2.58 (100) |
| 28. | 2.28 (100) | 2.57 (100) | 2.50 (100) |
| 29. | 2.40 (100) | 2.86 (100) | 2.78 (100) |
| 30. | 1.72 (100) | 2.11 (100) | 2.05 (100) |
| 31. | 1.63 (95) | 1.93 (100) | 1.81 (100) |
| 32. | 1.94 (100) | 2.29 (100) | 2.17 (100) |
| 33. | 2.47 (100) | 2.37 (100) | 2.51 (100) |
| 34. | 2.30 (100) | 2.66 (100) | 2.40 (100) |
| 35. | 1.64 (92) | 2.14 (100) | 2.18 (100) |
| 36. | 1.54 (90) | 1.88 (100) | 1.91 (95) |
| 37. | 2.39 (100) | 2.90 (100) | 2.77 (100) |
| 38. | 2.50 (100) | 2.84 (100) | 2.23 (100) |
| 39. | 1.92 (95) | 2.35 (100) | 2.19 (100) |
| 40. | 2.03 (100) | 2.46 (100) | 2.24 (100) |
| 41. | 1.73 (90) | 2.12 (100) | 2.15 (98) |
| 42. | 1.80 (95) | 2.09 (100) | 1.97 (100) |
| 43. | 1.77 (90) | 1.93 (100) | 2.04 (90) |
| 44. | 1.81 (100) | 2.07 (100) | 2.08 (100) |
| 45. | 1.44 (85) | 1.91 (98) | 1.83 (88) |
| 46. | 1.79 (90) | 2.03 (100) | 2.11 (100) |
| 47. | 1.82 (100) | 2.19 (100) | 2.06 (100) |
| 48. | 1.91 (100) | 2.33 (100) | 2.17 (100) |
| 49. | 2.16 (100) | 2.40 (100) | 2.23 (100) |
| 50. | 2.14 (100) | 2.58 (100) | 2.42 (100) |
| 51. | 1.97 (100) | 2.35 (100) | 2.11 (92) |
| 52. | 2.20 (100) | 2.64 (100) | 2.39 (100) |
| 53. | 1.88 (95) | 2.20 (100) | 2.07 (100) |
| 54. | 1.91 (100) | 2.18 (100) | 2.20 (100) |
| 55. | 1.80 (90) | 2.05 (100) | 2.09 (100) |
| 56. | 1.76 (85) | 1.90 (100) | 2.02 (92) |
| 57. | 1.71 (82) | 1.96 (98) | 1.94 (90) |
| 58. | 1.38 (78) | 1.81 (90) | 1.88 (80) |
| 59. | 1.40 (80) | 1.85 (90) | 1.79 (76) |
| 60. | 1.65 (84) | 2.01 (98) | 1.97 (90) |
| 61. | 1.98 (100) | 2.30 (100) | 2.15 (100) |
| 62. | 2.05 (100) | 2.42 (100) | 2.16 (100) |
| 63. | 1.95 (98) | 2.17 (100) | 2.02 (100) |
| 64. | 1.93 (100) | 2.14 (100) | 2.02 (100) |
| 65. | 1.70 (70) | 1.98 (100) | 2.03 (100) |
| 66. | 1.45 (78) | 1.88 (92) | 1.90 (85) |
| 67. | 1.71 (85) | 2.02 (100) | 2.05 (95) |
| 68. | 2.19 (100) | 2.54 (100) | 2.44 (100) |
| 69. | 1.94 (100) | 2.36 (100) | 2.17 (100) |
| 70. | 1.83 (90) | 2.09 (100) | 2.11 (100) |
| 71. | 1.92 (98) | 2.20 (100) | 2.04 (100) |
| 72. | 1.83 (95) | 2.04 (100) | 2.02 (100) |
| 73. | 1.97 (100) | 2.34 (100) | 2.21 (100) |
| 74. | 1.52 (80) | 1.86 (95) | 1.90 (85) |
| 75. | 1.98 (100) | 2.27 (100) | 2.18 (100) |
| 76. | 1.69 (86) | 1.94 (100) | 1.90 (92) |
| 77. | 1.58 (82) | 1.90 (95) | 1.88 (90) |
| 78. | 1.66 (90) | 2.02 (100) | 1.98 (95) |
| 79. | 1.80 (95) | 2.15 (100) | 2.10 (100) |
| 80. | 1.76 (80) | 2.04 (98) | 1.98 (85) |
| 81. | 1.36 (78) | 1.80 (90) | 1.85 (82) |
| 82. | 1.25 (80) | 1.61 (90) | 2.03 (90) |
| 83. | 1.40 (82) | 1.84 (95) | 1.83 (90) |

TABLE 3-continued

| Compound | (A) | (B) | (C) |
|---|---|---|---|
| 84. | 1.85 (100) | 2.07 (100) | 2.08 (100) |
| 85. | 1.50 (85) | 1.79 (95) | 1.93 (95) |
| 86. | 1.21 (80) | 1.40 (90) | 1.81 (85) |
| 87. | 1.27 (75) | 1.51 (90) | 1.76 (85) |
| 88. | 1.31 (80) | 1.51 (90) | 1.95 (90) |
| 89. | 1.26 (80) | 1.53 (95) | 1.83 (90) |
| 90. | 1.15 (80) | 1.37 (95) | 1.76 (90) |
| 91. | 1.54 (80) | 1.79 (90) | 2.07 (95) |
| 92. | 1.73 (90) | 2.01 (100) | 2.07 (100) |
| 93. | 1.39 (80) | 1.60 (95) | 1.94 (90) |
| 94. | 1.09 (80) | 1.21 (95) | 1.83 (90) |
| 95. | 1.76 (85) | 1.90 (100) | 2.02 (92) |
| 96. | 1.71 (82) | 1.96 (98) | 1.94 (90) |
| 97. | 1.93 (98) | 2.28 (100) | 2.26 (100) |
| 98. | 1.88 (95) | 2.36 (100) | 2.13 (100) |
| 99. | 1.41 (70) | 1.75 (90) | 1.93 (90) |
| 100. | 1.74 (90) | 2.05 (100) | 2.02 (100) |
| 101. | 1.82 (90) | 2.11 (100) | 2.08 (95) |
| 102. | 1.50 (80) | 1.71 (90) | 1.93 (90) |
| 103. | 1.59 (80) | 1.85 (90) | 2.07 (95) |
| 104. | 1.80 (90) | 1.93 (100) | 2.11 (100) |
| 105. | 1.50 (80) | 1.71 (95) | 2.04 (90) |
| 106. | 1.79 (85) | 1.94 (100) | 1.99 (90) |
| 107. | 1.81 (90) | 2.01 (100) | 2.10 (100) |
| 108. | 1.70 (80) | 1.96 (100) | 2.03 (100) |
| 109. | 1.68 (80) | 1.89 (100) | 2.11 (95) |
| 110. | 1.45 (75) | 1.84 (90) | 1.86 (85) |
| 111. | 1.54 (80) | 1.70 (95) | 1.89 (90) |
| 112. | 1.35 (75) | 1.81 (90) | 1.93 (80) |
| 113. | 1.47 (90) | 1.69 (100) | 1.95 (95) |
| 114. | 1.56 (100) | 1.81 (100) | 2.03 (100) |
| 115. | 1.49 (80) | 1.71 (95) | 1.96 (100) |
| 116. | 1.94 (100) | 2.33 (100) | 2.20 (100) |
| 117. | 1.86 (100) | 2.04 (100) | 2.07 (100) |
| 118. | 1.63 (85) | 1.87 (95) | 2.01 (100) |
| 119. | 1.47 (85) | 1.71 (100) | 1.89 (95) |
| 120. | 1.80 (95) | 2.15 (100) | 2.08 (100) |
| 121. | 1.52 (90) | 1.91 (100) | 1.84 (87) |
| 122. | 1.64 (97) | 2.03 (100) | 1.97 (90) |
| 123. | 1.85 (80) | 2.19 (100) | 2.13 (80) |
| 124. | 1.51 (72) | 1.98 (95) | 1.95 (77) |
| 125. | 1.36 (71) | 1.86 (90) | 1.79 (68) |
| 126. | 1.49 (82) | 2.05 (100) | 1.90 (85) |
| 127. | 1.77 (88) | 2.12 (100) | 2.04 (89) |
| 128. | 1.38 (75) | 1.90 (98) | 1.88 (74) |
| 129. | 1.60 (100) | 2.24 (100) | 2.17 (100) |
| 130. | 1.39 (75) | 1.91 (95) | 1.76 (78) |
| 131. | 1.24 (68) | 1.87 (90) | 1.78 (74) |
| 132. | 1.82 (100) | 2.24 (100) | 2.03 (100) |
| 133. | 2.09 (100) | 2.48 (100) | 2.27 (100) |
| 134. | 2.36 (100) | 2.75 (100) | 2.62 (100) |
| 135. | 1.98 (100) | 2.41 (100) | 2.25 (100) |
| 136. | 1.86 (100) | 2.20 (100) | 2.11 (100) |
| 137. | 1.82 (100) | 2.16 (100) | 2.05 (100) |
| 138. | 1.81 (100) | 2.17 (100) | 2.13 (100) |
| 139. | 1.75 (90) | 2.04 (100) | 1.97 (98) |
| 140. | 1.90 (100) | 2.23 (100) | 2.06 (100) |
| 141. | 2.01 (100) | 2.56 (100) | 2.49 (100) |
| 142. | 1.79 (100) | 2.11 (100) | 2.10 (100) |
| 143. | 1.98 (100) | 2.24 (100) | 2.15 (100) |
| 144. | 1.83 (95) | 2.19 (100) | 2.14 (100) |
| 145. | 1.92 (100) | 2.25 (100) | 2.23 (100) |
| 146. | 1.77 (95) | 2.08 (100) | 2.02 (100) |
| 147. | 2.04 (100) | 2.38 (100) | 2.26 (100) |
| 148. | 1.80 (98) | 2.12 (100) | 2.08 (100) |

As is seen from the above-shown test results, when 0.2% kerosene solution of each compound of the present invention is singly employed, each shows better knock-down effect than allethrin of pyrethroid conventionally used and the mortality rate of nearly 100%.

In case when piperonylbutoxide is added as synergyst, the knock-down and mortality effects are further enhanced. And also the solution of each compound of the present invention mixed with phthalthrin displays the synergystic effect on knock-down and mortality effects.

TEST EXAMPLE 3

Insecticidal effect by fumigation test

Mosquito incense sticks containing each 0.5% active ingredient were prepared and tested for the knock-down rate of mosquitoes (Culex Pipiens Pallens). These test were carried out in accordance with the procedure described by Nagasawa, Katsuda and others in "Bochu-Kagaku" Vol. 16, page 176 (1951). The relative effect values of these mosquito incense sticks are as follows:

TABLE 4

| Compound | Probit 4 | Probit 5 | Probit 6 |
|---|---|---|---|
| Allethrin | 1.00 | 1.00 | 1.00 |
| 1. | 1.37 | 1.40 | 1.43 |
| 2. | 1.51 | 1.56 | 1.59 |
| 3. | 1.25 | 1.28 | 1.31 |
| 4. | 1.70 | 1.74 | 1.79 |
| 5. | 1.52 | 1.55 | 1.58 |
| 7. | 1.60 | 1.63 | 1.66 |
| 8. | 1.62 | 1.65 | 1.69 |
| 9. | 1.65 | 1.68 | 1.71 |
| 11. | 1.81 | 1.85 | 1.88 |
| 13. | 1.92 | 1.97 | 2.03 |
| 14. | 2.46 | 2.50 | 2.54 |
| 15. | 2.13 | 2.16 | 2.20 |
| 16. | 1.71 | 1.75 | 1.79 |
| 17. | 1.84 | 1.86 | 1.89 |
| 18. | 1.56 | 1.59 | 1.61 |
| 19. | 2.01 | 2.06 | 2.09 |
| 20. | 1.75 | 1.78 | 1.80 |
| 22. | 2.19 | 2.22 | 2.26 |
| 24. | 1.70 | 1.74 | 1.78 |
| 25. | 1.68 | 1.72 | 1.76 |
| 27. | 2.25 | 2.31 | 2.37 |
| 28. | 2.10 | 2.13 | 2.18 |
| 29. | 1.84 | 1.86 | 1.90 |
| 31. | 1.96 | 1.99 | 2.04 |
| 32. | 1.70 | 1.73 | 1.76 |
| 33. | 1.64 | 1.68 | 1.70 |
| 34. | 1.60 | 1.63 | 1.68 |
| 35. | 1.41 | 1.45 | 1.47 |
| 36. | 1.32 | 1.33 | 1.37 |
| 38. | 1.50 | 1.51 | 1.54 |
| 41. | 1.45 | 1.49 | 1.53 |
| 45. | 1.19 | 1.21 | 1.24 |
| 49. | 1.57 | 1.61 | 1.63 |
| 52. | 1.49 | 1.53 | 1.57 |
| 54. | 1.34 | 1.39 | 1.42 |
| 58. | 1.16 | 1.18 | 1.22 |
| 67. | 1.33 | 1.37 | 1.41 |
| 68. | 1.56 | 1.59 | 1.62 |
| 70. | 1.45 | 1.48 | 1.52 |
| 73. | 1.56 | 1.58 | 1.61 |
| 74. | 1.31 | 1.35 | 1.38 |
| 75. | 1.49 | 1.53 | 1.56 |
| 78. | 1.27 | 1.30 | 1.35 |
| 79. | 1.11 | 1.14 | 1.20 |
| 82. | 1.23 | 1.29 | 1.33 |
| 84. | 1.28 | 1.30 | 1.34 |
| 85. | 1.28 | 1.33 | 1.37 |
| 87. | 1.37 | 1.41 | 1.46 |
| 90. | 1.09 | 1.15 | 1.24 |
| 92. | 1.40 | 1.44 | 1.47 |
| 93. | 1.25 | 1.31 | 1.34 |
| 96. | 1.20 | 1.23 | 1.29 |
| 101. | 1.46 | 1.49 | 1.53 |
| 103. | 1.29 | 1.34 | 1.40 |
| 106. | 1.22 | 1.28 | 1.30 |
| 108. | 1.20 | 1.25 | 1.28 |
| 111. | 1.36 | 1.40 | 1.45 |
| 114. | 1.33 | 1.36 | 1.40 |
| 116. | 1.48 | 1.50 | 1.54 |
| 118. | 1.20 | 1.21 | 1.28 |
| 120. | 1.31 | 1.35 | 1.38 |
| 124. | 1.37 | 1.40 | 1.42 |
| 127. | 1.43 | 1.47 | 1.50 |
| 130. | 1.19 | 1.23 | 1.26 |
| 135. | 1.56 | 1.60 | 1.63 |
| 136. | 1.69 | 1.71 | 1.75 |
| 137. | 1.68 | 1.71 | 1.74 |

TABLE 4-continued

| Compound | Probit 4 | Probit 5 | Probit 6 |
|---|---|---|---|
| 141. | 1.52 | 1.55 | 1.58 |
| 146. | 1.49 | 1.52 | 1.56 |

In the table 4, the knock-down ratios of the mosquitoes in Probit 4, 5 and 6 are 16%, 50% and 84% respectivelly and the relative activity is calculated from the time required for attaining said knock-down rates. From the above results, it can be seen that the compounds of the present invention show the more excellent effect than allethrin and they can be also used as an active ingredient of a fumigant.

TEST EXAMPLE 4

Insecticidal test by topical application method

Acetone solutions each containing a given amount of allethrin and each compound of the present invention, and those containing said active ingredients together with piperonyl butoxide twice the quantity of the active ingredient are prepared. Each solution is applied to the breast and the back of house fly by means of microsyringe. Relative mortality of the compounds in comparison with allethrin and the synergistic effect by piperonyl butoxide are examined based on the mortality at 24 hrs. after the application. The result is indicated in the table below.

TABLE 5

| Compound | Relative mortality | Relative mortality when synergist added | Rate of enhanced mortality |
|---|---|---|---|
| Allethrin | 1.00 | 2.35 | 2.4 |
| 1. | 4.76 | 17.14 | 3.6 |
| 2. | 6.80 | 22.44 | 3.3 |
| 4. | 5.52 | 22.08 | 4.0 |
| 6. | 5.96 | 26.82 | 4.5 |
| 8. | 4.52 | 17.18 | 3.8 |
| 9. | 7.13 | 29.23 | 4.1 |
| 10. | 5.35 | 22.47 | 4.2 |
| 11. | 8.76 | 31.54 | 3.6 |
| 13. | 9.26 | 33.34 | 3.6 |
| 14. | 5.34 | 21.89 | 4.1 |
| 15. | 4.81 | 14.43 | 3.0 |
| 16. | 6.53 | 24.16 | 3.7 |
| 17. | 3.90 | 13.26 | 3.4 |
| 18. | 6.47 | 27.17 | 4.2 |
| 20. | 5.65 | 19.78 | 3.5 |
| 22 | 4.62 | 13.40 | 2.9 |
| 24. | 7.02 | 23.87 | 3.4 |
| 30. | 4.49 | 17.96 | 4.0 |
| 33. | 6.38 | 22.33 | 3.5 |
| 34. | 6.14 | 19.65 | 3.2 |
| 40. | 5.33 | 20.79 | 3.9 |
| 61. | 5.91 | 21.87 | 3.7 |
| 65. | 3.77 | 14.70 | 3.9 |
| 68. | 6.04 | 24.16 | 4.0 |
| 75. | 4.62 | 17.56 | 3.8 |
| 80. | 3.54 | 11.68 | 3.3 |
| 84. | 4.82 | 17.83 | 3.7 |
| 90. | 4.13 | 16.11 | 3.9 |
| 94. | 3.76 | 13.54 | 3.6 |
| 103. | 4.05 | 14.99 | 3.7 |
| 106. | 5.11 | 16.86 | 3.3 |
| 111. | 5.74 | 22.96 | 4.0 |
| 114. | 4.54 | 16.34 | 3.6 |
| 120. | 4.83 | 18.35 | 3.8 |
| 123. | 4.50 | 14.85 | 3.3 |
| 128. | 3.49 | 14.66 | 4.2 |
| 132. | 5.71 | 19.99 | 3.5 |
| 139. | 4.43 | 15.06 | 3.4 |
| 146. | 5.05 | 18.18 | 3.6 |

Addition of piperonyl butoxide enhances the insecticidal effect of the compounds of the present invention more than 3 times as high. This means that high mortality can be attained by a smaller amount of the compounds of the present invention.

REFERENCE EXAMPLE 1

Each 0.2 parts of Compounds (1), (4), (8), (13), (33) and (75) of the present invention is dissolved in sufficient kerosene to form 100 parts of 0.2% solution.

REFERENCE EXAMPLE 2

Each 0.2 parts of Compounds (2), (5), (9), (14), (34) and (76) of the present invention and 0.8 parts of piperonylbutoxide are dissolved in sufficient kerosene to form 100 parts of solution.

REFERENCE EXAMPLE 3

Each 20 parts of Compounds (16), (36), (78) and (136) of the present invention, 10 parts of Solpol SM-200 (tradename of Toho Chemical Co.) and 70 parts of xylene are mixed with stirring to form 20% emulsifiable concentrate.

REFERENCE EXAMPLE 4

Each 0.4 parts of Compounds (19), (42) and (84) of the present invention, 0.1 part of resmethrin and 1.5 parts of octachlorodipropyl ether are dissolved in 28 parts of rectified kerosene. The solution is charged in an aerosol vessel and a jet-valve is attached to the vessel, through which 70 parts of propellant (liquefied petroleum gas) are compressed into the vessel to obtain an aerosol preparation.

REFERENCE EXAMPLE 5

Each 0.5 g of Compounds (7), (22), (51) and (93) of the present invention and 0.5 g of BHT are uniformly mixed with 99.0 g of substrate for mosquito incense sticks such as pyrethrum extract powder, powdered wood and starch, etc. The resulting substance is molded into mosquito incense stick by a publicly known process.

REFERENCE EXAMPLE 6

Each 0.4 g of Compounds (59) and (101) of the present invention and 1.0 g of MGK-5026 are uniformly blended with 98.6 g of substrate for mosquito incense stick. The resulting substance is molded into mosquito incense stick by a publicly known process.

REFERENCE EXAMPLE 7

Each 3 parts of Compounds (10), (25), (67) and (116) of the present invention and 97 parts of clay are blended well and pulverized to obtain 3% powder.

REFERENCE EXAMPLE 8

Each 40 parts of Compounds (6), (74) and (104) of the present invention, 35 parts of diatomaceous earth, 20 parts of clay, 3 parts of laurylsulfonic acid salt and 2 parts of carboxymethylcellulose are crushed and blended to form wettable powder.

TEST EXAMPLE 4

Each emulsifiable concentrate containing Compounds (2), (5), (8), (13), (14), (16), (26), (32), (35), (36), (39), (48), (53), (57), (62), (66), (69), (73), (77), (78), (81), (90), (95), (99), (104), (108), (115), (117), (119), (123), (128), (132), (136), and (141) of the present invention, which are prepared by the method mentioned in Reference Example 3, is diluted with water to prepare 1/1000 solution. 100 l/10a of the solution is sprayed onto Japanese radish leaves at the 5-6 leaf stage, on which a lot of green peach aphid (Myzus persicae Sulzer) are grown all over the surface. After 2 days, the green peach aphides decrease to less than 1/10 in each case when compared to those before spraying.

TEST EXAMPLE 5

One day before applying insecticide, about 200 aphides (Aphis craccivora Koch) are put on each broad bean plant (Vicia faba L) in a pot. Each wettable powder containing Compounds (1), (4), (6), (7), (14), (17), (18), (30), (34), (38), (46), (51), (56), (59), (67), (70), (74), (76), (80), (88), (93), (98), (101), (104), (109), (112), (117), (120), (124), (127), (130), (133), (138) and (144) of the present invention, which are prepared by the method of Reference Example 8 is diluted with water to prepare 1/4000 solution. Each 10 ml/pot of the diluted solution is sprayed on the bean leaves which swarm with aphides by means of compressed air spray. After two days, any increase of damage is not observed in each case.

TEST EXAMPLE 6

Each emulsifiable concentrate containing Compounds (1), (3), (4), (8), (9), (10), (12), (13), (15), (16), (21), (23), (33), (36), (44), (49), (55), (57), (64), (71), (73), (75), (78), (85), (91), (97), (100), (106), (113), (115), (119), (126), (134), (136), (137), (143), and (147) of the present invention, which is prepared by the method in Reference Example 3, is diluted with water to prepare 1/2000 solution. Cabbage leaves are immersed in the solution for about five seconds. After the coating is dried, the leaves are put in a glass vessel in which 10 sound larvae of cabbage armyworm are settled. The larvae are supplied twice at the date when the test leaves are prepared and 5 days after that date. Mortality of Compounds tested after 24 hrs. is listed as follows:

TABLE 6

| Compound | First day | 5th day |
|---|---|---|
| Salithion | 40 (%) | 5 (%) |
| 1. | 85 | 70 |
| 3. | 85 | 75 |
| 4. | 85 | 70 |
| 8. | 100 | 100 |
| 9. | 100 | 100 |
| 10. | 100 | 100 |
| 12. | 100 | 80 |
| 13. | 100 | 85 |
| 15. | 100 | 80 |
| 16. | 100 | 100 |
| 21. | 95 | 80 |
| 23. | 100 | 100 |
| 33. | 100 | 100 |
| 36. | 100 | 100 |
| 44. | 100 | 95 |
| 49. | 100 | 100 |
| 55. | 100 | 95 |
| 57. | 95 | 90 |
| 64. | 100 | 100 |
| 71 | 100 | 95 |
| 73. | 100 | 100 |
| 75. | 100 | 100 |
| 78. | 100 | 100 |
| 85. | 100 | 90 |
| 91. | 100 | 90 |
| 97. | 100 | 95 |
| 100. | 100 | 95 |
| 106. | 100 | 100 |
| 113. | 100 | 85 |
| 115. | 95 | 80 |
| 119. | 95 | 85 |

TABLE 6-continued

| Compound | First day | 5th day |
|---|---|---|
| 126. | 90 | 80 |
| 134. | 95 | 85 |
| 136. | 100 | 95 |
| 137. | 100 | 95 |
| 143. | 95 | 85 |
| 147. | 90 | 85 |

TEST EXAMPLE 7

Each powder containing (3), (6), (11), (13), (16), (18), (23), (24), (25), (26), (32), (37), (42), (47), (54), (60), (63), (68), (71), (74), (79), (84), (89), (96), (102), (105), (110), (116), (120), (127) and (131) which is prepared by the Reference Example 7 is uniformly sprinkled at the ratio of 2 g/m² on the bottom of a tall glass vessel having a diameter of 14 cm and then butter is coated on the wall of the vessel leaving the portion of 1 cm height from the bottom. A group consisting of 10 imagines of Blattella germanicas are placed on the bottom of the vessel. After the group is put into contact with the powder for 30 minutes, it is transferred into a clean vessel. After three days, more than 80% of germanicas are killed with any of powders.

What is claimed is:

1. Cyclopropane carboxylic acid ester derivatives and optical and geometrical isomers thereof expressed by the general formula:

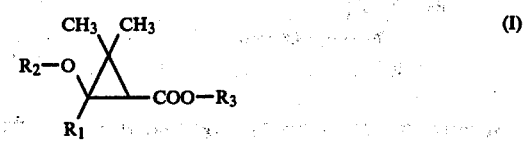

wherein $R_1$ represents hydrogen atom or methyl group, $R_2$ represents alkyl group, alkenyl group, haloalkyl group, haloalkenyl group having 1-6 carbon atoms and a group selected from groups of the general formulae (II), (III) and (IV):

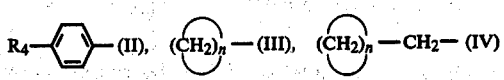

in which n is an integer of 2-5, $R_4$ represents methyl group, chlorine atom or methoxy group, and $R_3$ represents a group selected from the groups of the general formulae (V), (VI), (VII), (VIII), (IX) and (X):

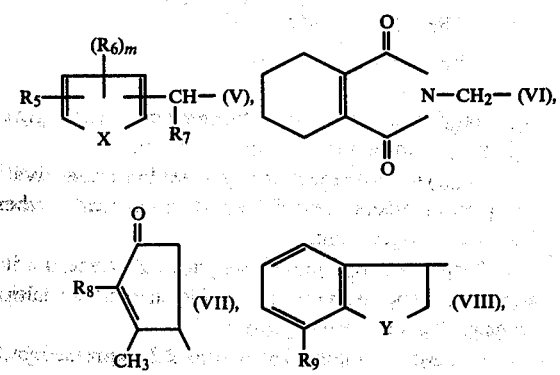

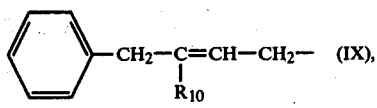  (IX),

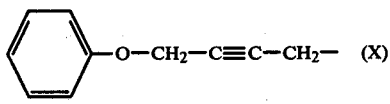  (X)

in which X represents oxygen atom or vinylene group, $R_5$ represents allyl group, propargyl group, benzyl group, phenoxy group or 2,2-dichlorovinyloxy group, $R_6$ represents hydrogen atom, methyl group or haloen atom, $R_7$ represents hydrogen atom, cyano group, ethynyl group or trifluoromethyl group and m is an integer of 1-2, $R_8$ represents allyl group or pentadienyl group, Y represents oxygen atom or methylene group, $R_9$ represents hydrogen atom, methyl group, allyl group or halogen atom and $R_{10}$ represents methyl group or halogen atom.

2. Cyclopropane carboxylic acid ester derivatives and optical and geometrical isomers thereof expressed by the general formula:

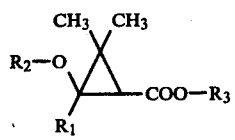  (I)

wherein $R_1$ represents hydrogen atom or methyl group, $R_2$ represents alkyl group, alkenyl group, haloalkyl group, haloalkenyl group having 1-6 carbon atoms and a group selected from the groups of the general formulae (II), (III) and (IV):

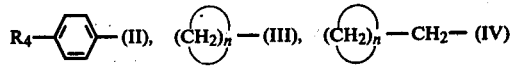

in which n is an integer of 2-5, $R_4$ represents methyl group, chlorine atom or methoxy group, and $R_3$ represents the general formula:

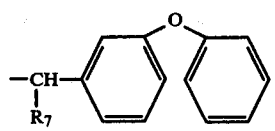

wherein $R_7$ represents hydrogen atom, cyano group, ethynyl group or trifluoromethyl group.

3. The cyclopropane carboxylic acid ester derivatives and steric isomers thereof set forth in claim 1 wherein $R_1$ is a hydrogen atom.

4. The cyclopropane carboxylic acid ester derivatives and the steric isomers thereof claimed in claim 1 wherein $R_1$ is a methyl group.

5. Compound claimed in claim 2 expressed by the formula:

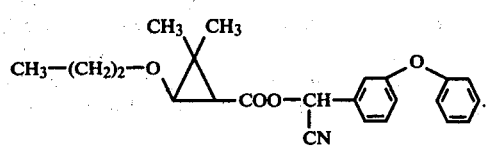

6. Compound claimed in claim 2 expressed by the formula:

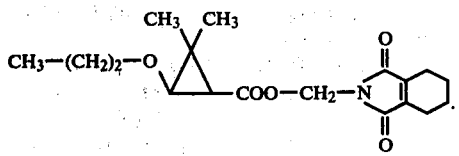

7. Compound claimed in claim 2 expressed by the formula:

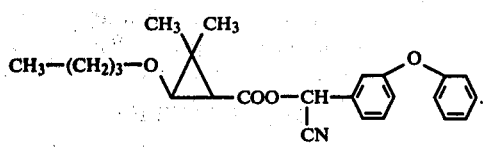

8. Compound claimed in claim 2 expressed by the formula:

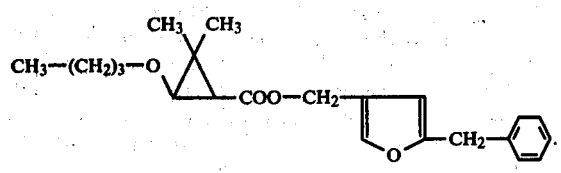

9. Compound claimed in claim 2 expressed by the formula:

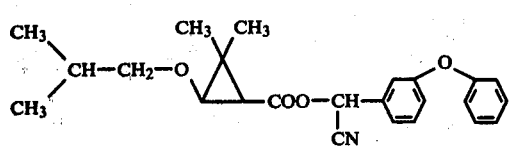

10. Compound claimed in claim 2 expressed by the formula:

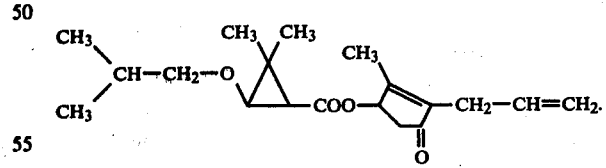

11. Compound claimed in claim 2 expressed by the formula:

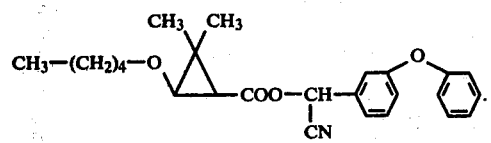

12. Compound claimed in claim 2 expressed by the formula:

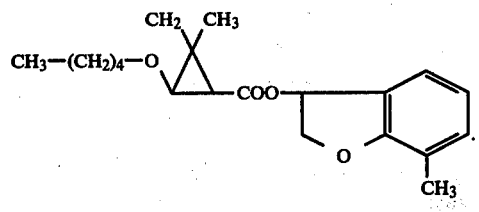

13. Compound claimed in claim 2 expressed by the formula:

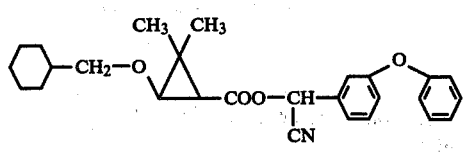

14. Compound claimed in claim 3 expressed by the formula:

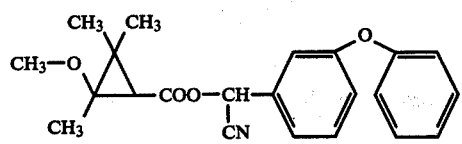

15. Compound claimed in claim 3 expressed by the formula:

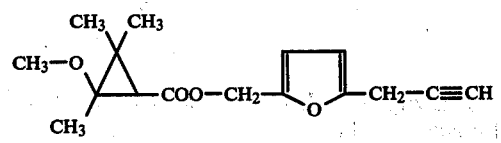

16. An insecticidal composition comprising an inert carrier and an insecticidally effective amount of a compound as set forth in claim 1.

17. An insecticidal composition according to claim 16 which includes as an auxiliary agent a syngergistically effective amount of a compound selected from the group consisting of piperonyl butoxide, octachlorodipropyl ether, N-octylbicycloheptene dicarboximide and N-octyl-1-isopropyl-4-methylbicyclo-[2,2,2]-oct-5-en-2,3-dicarboxyimide.

18. A compound of the formula

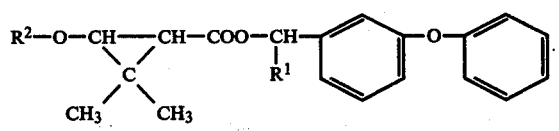

wherein,
$R^1$ is hydrogen or cyano; and
$R^2$ is lower alkyl of 1 to 6 carbon atoms, lower haloalkyl of 1 to 6 carbon atomes, lower alkenyl of 2 to 6 carbon atoms, lower haloalkenyl of 2 to 6 carbon atoms and a group selected from the groups of the general formulae (II), (III), and (IV):

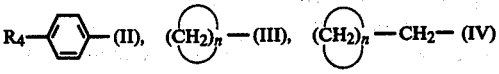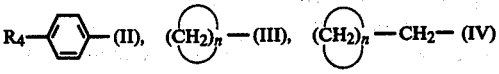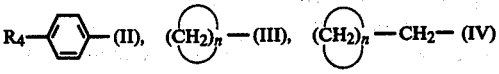

in which n is an integer of 2–5, $R_4$ is a methyl group, chlorine atom or methoxy group.

19. A method for combatting pests which comprises treating said pest with a pesticidally effective amount of a compound of the formula amount of a

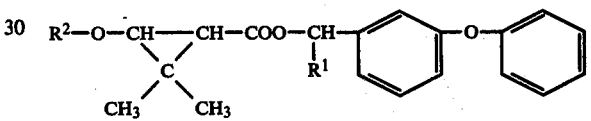

wherein,
$R^1$ is a hydrogen or cyano; and
$R^2$ is a lower alkyl of 1 to 6 carbon atoms, lower haloalkyl of 1 to 6 carbon atoms, lower alkenyl of 2 to 6 carbon atoms, lower haloalkenyl of 2 to 6 carbon atoms and a group selected from the groups of the general formulae (II), (III), and (IV):

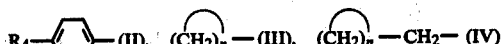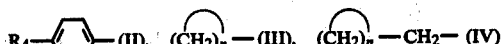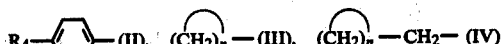

in which n is an integer of 2–5, $R_4$ is a methyl group, chlorine atom or methoxy group.

* * * * *